US006416950B1

(12) United States Patent
Lohse et al.

(10) Patent No.: US 6,416,950 B1
(45) Date of Patent: Jul. 9, 2002

(54) DNA-PROTEIN FUSIONS AND USES THEREOF

(75) Inventors: Peter Lohse, Weston; Markus Kurz, West Newton, both of MA (US)

(73) Assignee: Phylos, Inc., Lexington, MA (US)

( * ) Notice: Subject to any disclaimer, the term of this patent is extended or adjusted under 35 U.S.C. 154(b) by 0 days.

(21) Appl. No.: 09/453,190

(22) Filed: Dec. 2, 1999

Related U.S. Application Data

(60) Provisional application No. 60/110,549, filed on Dec. 2, 1998.

(51) Int. Cl.⁷ .......................... C12Q 1/68; C12P 19/34; C12N 15/00; A01N 43/04; C07H 21/02
(52) U.S. Cl. ..................... 435/6; 435/91.1; 435/91.53; 435/320.1; 436/6; 514/44; 536/23.1; 536/23.5
(58) Field of Search ........................ 435/6, 91.1, 91.53, 435/320.1; 436/6; 514/44; 536/23.1, 23.5

(56) References Cited

U.S. PATENT DOCUMENTS

| | | | | |
|---|---|---|---|---|
| 4,587,044 | A | 5/1986 | Miller et al. .................. | 530/211 |
| 5,270,163 | A | 12/1993 | Gold .............................. | 435/6 |
| 5,360,714 | A | * 11/1994 | Seeger ........................... | 435/5 |
| 5,422,253 | A | * 6/1995 | Dahlberg et al. ......... | 435/91.53 |
| 5,541,061 | A | 7/1996 | Fodor et al. .................... | 435/6 |
| 5,547,839 | A | 8/1996 | Dower et al. ................... | 435/6 |
| 5,627,024 | A | 5/1997 | Maruyama et al. ............ | 435/5 |
| 5,643,768 | A | 7/1997 | Kawasaki ................. | 435/91.21 |
| 5,658,754 | A | 8/1997 | Kawasaki .................. | 435/69.1 |
| 5,789,208 | A | 8/1998 | Sharon .................... | 435/91.41 |
| 5,800,992 | A | 9/1998 | Fodor et al. .................... | 435/6 |
| 5,843,701 | A | 12/1998 | Gold et al. .................... | 435/68 |
| 5,849,878 | A | 12/1998 | Cantor et al. ............. | 530/391.9 |
| 5,962,425 | A | * 10/1999 | Walder et al. ................. | 514/44 |
| 5,965,133 | A | 10/1999 | Cantor et al. ............ | 424/179.1 |
| 5,985,757 | A | 11/1999 | Wickens et al. ............... | 435/6 |

FOREIGN PATENT DOCUMENTS

| | | | |
|---|---|---|---|
| DE | 19646372 | 11/1996 | |
| WO | WO 91/05058 | 4/1991 | |
| WO | WO 92/02536 | 2/1992 | |
| WO | WO 93/03172 | 2/1993 | |
| WO | WO 98/16636 | 4/1998 | |
| WO | WO 98/31700 | * 7/1998 | .................... 435/6 |
| WO | WO 98/37186 | 8/1998 | |

OTHER PUBLICATIONS

Trask et al., "Stabilization of Type I Topoisomerase–DNA Covalent Complexes by Actinomycin D," *Proc. Natl. Acad. Sci. USA* 85:1417–1421 (1988).

Zhen et al.,"Psoralen photofootprinting of protein–binding sites on DNA", *FEBS Letters*, vol. 229 (1), pp. 73–76, Feb. 1988.*

Brenner and Lerner, "Encoded Combinatorial Chemistry," *Proc. Natl. Acad. Sci. USA* 89:5381–5383 (1992).

Ghosh et al., "Synthesis of 5'–Oligonucleotide Hydrazide Derivatives and Their Use in Preparation of Enzyme–Nucleic Acid Hybridization Probes," *Analytical BioChemistry* 178:43–51 (1989).

Hanes and Plückthun, "In vitro Selection and Evolution of Functional Proteins by Using Ribosome Display," *Proc. Natl. Acad. Sci. USA* 94:4937–4942 (1997).

He and Taussig, "Antibody–Ribosome–mRNA (ARM) Complexes as Efficient Selection Particles for in vitro Display and Evolution of Antibody Combining Sites," *Nucleic Acids Research* 25:5132–5134 (1997).

Lemaitre et al., "Specific Antiviral Activity of a Poly(L–l–ysine)–Conjugated Oligodeoxyribonucleotide Sequence Complementary to Vesiclular Stomatitis Virus N Protein mRNA Initiation Site," *Proc. Natl. Acad. Sci. USA* 84: 648–652 (1987).

Nielsen et al., "Synthetic Methods for the Implementation of Encoded Combinatorial Chemistry," *J. Am. Chem. Soc.* 115:9812–9813 (1993).

Niemeyer et al., "Oligonucleotide–Directed Self–Assembly of Proteins: Semisynthetic DNA—Streptavidin Hybrid Molecules as Connectors for the Generation of Macroscopic Arrays and the Construction of Supramolecular Bioconjugates," *Nucleic Acids Research* 22:5530–5539 (1994).

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Research* 17:285–299 (1989).

Proudnikev et al., "Chemical Methods of DNA and RNA Fluorescent LabeLing," *Nucleic Acids Research* 24:4535–4542 (1996).

Roberts and Szostak, "RNA–Peptide Fusions for the in vitro Selection of Peptides and Proteins," *Proc. Natl. Acad. Sci. USA* 94:12297–12302 (1997).

Trask and Muller, "Stabilization of Type I Topoisomerase—DNA Covalent Complexes by Actinomycin D," *BioChemistry* 85:1417–1421 (1988).

* cited by examiner

*Primary Examiner*—W. Gary Jones
*Assistant Examiner*—Arun K. Chakrabarti
(74) *Attorney, Agent, or Firm*—Clark & Elbing LLP

(57) ABSTRACT

Disclosed herein are molecules that include a deoxyribonucleic acid (DNA) covalently bonded to a protein and uses thereof.

14 Claims, 20 Drawing Sheets

Pu   PUROMYCIN
∿   RNA
—   DNA
•   LIGATION SITE

DNA-PROTEIN FUSIONS AND USES THEREOF

CROSS REFERENCE TO RELATED APPLICATIONS

This application claims the benefit of the filing date of co-pending application, U.S. Ser. No. 60/110,549, filed Dec. 2, 1998.

BACKGROUND OF THE INVENTION

In general, the invention features DNA-protein fusions and their uses, particularly for the selection of desired proteins and their corresponding nucleic acid sequences.

Recently, a combinatorial method was developed for the isolation of proteins with desired properties from large pools of proteins (Szostak et al., U.S. Ser. No. 09/007,005; Szostak et al., WO98/31700; Roberts & Szostak, Proc. Natl. Acad. Sci. USA (1997) vol. 94, p. 12297–12302). By this method, the protein portion is linked to its encoding RNA by a covalent chemical bond. Due to the covalent nature of this linkage, selection experiments are not limited to the extremely mild reaction conditions that must be used for approaches that involve non-covalent complex formation such as ribosome display (Hanes & Plückthun, Proc. Natl. Acad. Sci. USA (1997) vol. 94, p. 4937–4942; He & Taussig, Nucl. Acids Res. (1997) vol. 25, p 5132–5143). However, precautions do need to be taken during the selection process to minimize RNA degradation, since the accidental cleavage of ribo-bonds can result in the irreversible loss of encoded information. For this reason, these selection procedures are typically carried out using reaction media and equipment that are free of ribonucleases or other deleterious contaminants.

SUMMARY OF THE INVENTION

The present invention provides methods for covalently tagging proteins with their encoding DNA sequences. These DNA-protein fusions, which may be used in molecular evolution and recognition techniques, are chemically more stable than RNA-protein fusions and therefore provide a number of advantages (as discussed in more detail below).

Accordingly, in general, the invention features methods for generating DNA-protein fusions. A first method involves: (a) linking a nucleic acid primer to an RNA molecule (preferably, at or near the RNA 3' end), the primer being bound to a peptide acceptor (for example, puromycin); (b) translating the RNA to produce a protein product, the protein product being covalently bound to the primer; and (c) reverse transcribing the RNA to produce a DNA-protein fusion.

A second method involves: (a) generating an RNA-protein fusion; (b) hybridizing a nucleic acid primer to the fusion (preferably, at or near the RNA 3' end); and (c) reverse transcribing the RNA to produce a DNA-protein fusion.

In a preferred embodiment of the above methods, the method may further involve treating the product of step (c) to remove the RNA (for example, by contacting the product of step (c) with RNase H under conditions sufficient to digest the RNA). In additional preferred embodiments, the nucleic acid primer is a DNA primer; the translating step is carried out in vitro; and the nucleic acid primer has a hairpin structure. In addition, the primer may further include a photocrosslinking agent, such as psoralen, and the primer may be crosslinked to an oligonucleotide which is bound to a peptide acceptor or, alternatively, may be hybridized to the RNA molecule, followed by a linking step that is carried out by photocrosslinking.

In related aspects, the invention also features a molecule including a DNA covalently bonded to a protein (preferably, of at least 10 amino acids) through a peptide acceptor (for example, puromycin), as well as a molecule including a DNA covalently bonded to a protein, in which the protein includes at least 10 amino acids.

In preferred embodiments of both of these aspects, the protein includes at least 30 amino acids, more preferably, at least 100 amino acids, and may even include at least 200 or 250 amino acids. In other preferred embodiments, the protein is encoded by the DNA and is preferably entirely encoded by the DNA; the molecule further includes a ribonucleic acid covalently bonded to the DNA; the protein is encoded by the ribonucleic acid; and the DNA is double stranded.

In another related aspect, the invention features a population of at least $10^5$, and preferably, at least $10^{14}$, DNA-protein fusions of the invention, each fusion including a DNA covalently bonded to a protein.

In addition, the invention features selection methods which utilize the DNA-protein fusions described herein. A first selection method involves the steps of: (a) providing a population of DNA-protein fusions, each including a DNA covalently bonded to a candidate protein; and (b) selecting a desired DNA-protein fusion, thereby selecting the desired protein or DNA.

A second selection method involves the steps of: (a) producing a population of candidate DNA-protein fusions, each including a DNA covalently bonded to a candidate protein and having a candidate protein coding sequence which differs from a reference protein coding sequence; and (b) selecting a DNA-protein fusion having an altered function, thereby selecting the protein having the altered function or its encoding DNA.

In preferred embodiments, the selection step involves either binding of the desired protein to an immobilized binding partner or assaying for a functional activity of the desired protein. In addition, the method may further involve repeating steps (a) and (b).

In a final aspect, the invention features a solid support including an array of immobilized molecules, each including a covalently-bonded DNA-protein fusion of the invention. In a preferred embodiment, the solid support is a microchip.

As used herein, by a "population" is meant $10^5$ or more molecules (for example, DNA-protein fusion molecules). Because the methods of the invention facilitate selections which begin, if desired, with large numbers of candidate molecules, a "population" according to the invention preferably means more than $10^7$ molecules, more preferably, more than $10^9$, $10^{13}$, or $10^{14}$ molecules, and, most preferably, more than $10^{15}$ molecules.

By "selecting" is meant substantially partitioning a molecule from other molecules in a population. As used herein, a "selecting" step provides at least a 2-fold, preferably, a 30-fold, more preferably, a 100-fold, and, most preferably, a 1000-fold enrichment of a desired molecule relative to undesired molecules in a population following the selection step. A selection step may be repeated any number of times, and different types of selection steps may be combined in a given approach.

By a "protein" is meant any two or more naturally occurring or modified amino acids joined by one or more peptide bonds. "Protein" and "peptide" are used interchangeably herein.

By "RNA" is meant a sequence of two or more covalently bonded, naturally occurring or modified ribonucleotides. One example of a modified RNA included within this term is phosphorothioate RNA.

By "DNA" is meant a sequence of two or more covalently bonded, naturally occurring or modified deoxyribonucleotides.

By a "nucleic acid" is meant any two or more covalently bonded nucleotides or nucleotide analogs or derivatives. As used herein, this term includes, without limitation, DNA, RNA, and PNA.

By a "peptide acceptor" is meant any molecule capable of being added to the C-terminus of a growing protein chain by the catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Ellman et al., Meth. Enzymol. 202:301, 1991), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimetics of the combined nucleotide-amino acid structure.

By an "altered function" is meant any qualitative or quantitative change in the function of a molecule.

By "binding partner," as used herein, is meant any molecule which has a specific, covalent or non-covalent affinity for a portion of a desired DNA-protein fusion. Examples of binding partners include, without limitation, members of antigen/antibody pairs, protein/inhibitor pairs, receptor/ligand pairs (for example cell surface receptor/ligand pairs, such as hormone receptor/peptide hormone pairs), enzyme/substrate pairs (for example, kinase/substrate pairs), lectin/carbohydrate pairs, oligomeric or heterooligomeric protein aggregates, DNA binding protein/DNA binding site pairs, RNA/protein pairs, and nucleic acid duplexes, heteroduplexes, or ligated strands, as well as any molecule which is capable of forming one or more covalent or non-covalent bonds (for example, disulfide bonds) with any portion of a DNA-protein fusion.

By a "solid support" is meant, without limitation, any column (or column material), bead, test tube, microtiter dish, solid particle (for example, agarose or sepharose), microchip (for example, silicon, silicon-glass, or gold chip), or membrane (for example, the membrane of a liposome or vesicle) to which an affinity complex may be bound, either directly or indirectly (for example, through other binding partner intermediates such as other antibodies or Protein A), or in which an affinity complex may be embedded (for example, through a receptor or channel).

The present invention provides methods for the creation of fusions between proteins and their encoding cDNAs. These constructs possess greatly enhanced chemical stability, first, due to the DNA component of the fusion and, second, due to the covalent bond linking of the DNA and protein moieties. These properties allow for easier handling of the fusion products and thereby allow selection and recognition experiments to be carried out under a range of reaction conditions. In addition, the present invention facilitates applications where a single-stranded nucleic acid portion is mandatory, for example, in hybridization assays in which the coding fusions are immobilized to a solid support. In addition, incubations may be performed under more rigorous conditions, involving high pH, elevated concentrations of multivalent metal ions, prolonged heat treatment, and exposure to various biological materials. Finally, single-stranded DNA is relatively resistant to secondary structure formation, providing a great advantage for techniques involving or requiring nucleic acid hybridization steps.

In addition, the methods of the present invention allow for the production of fusions involving DNA and protein components of any length, as well as fusion libraries of high complexity.

Other features and advantages of the invention will be apparent from the following detailed description, and from the claims.

DETAILED DESCRIPTION

There are now provided below a number of exemplary techniques for the production of DNA-protein fusions, and descriptions for their use. These examples are provided for the purpose of illustrating, and not limiting, the invention.

Figure 1:
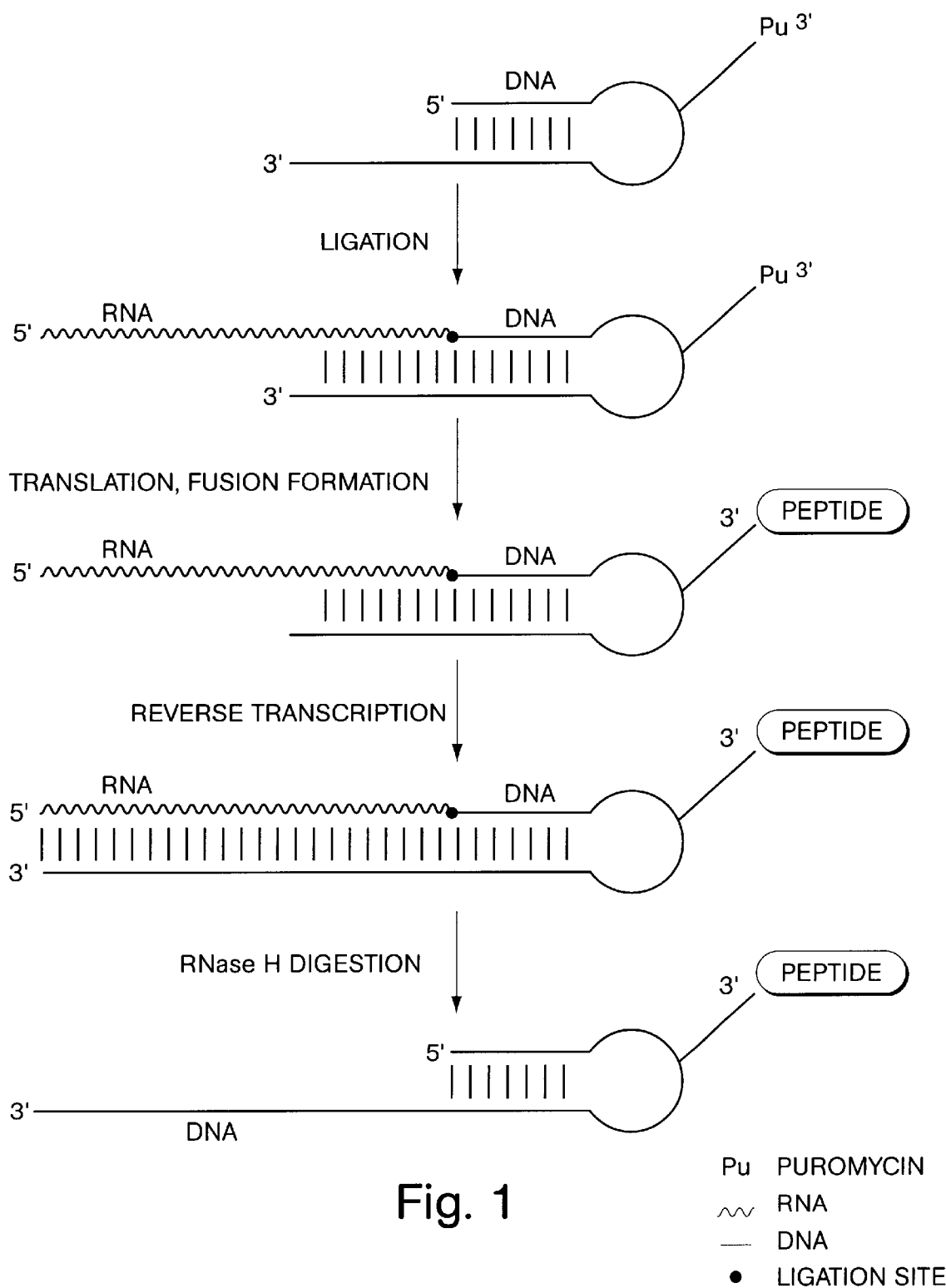
FIG. 1 is a schematic illustration of a method for the generation of DNA-Protein fusions (Type A1) that involves ligation of a puromycin-modified DNA hairpin-like structure to an mRNA molecule.
Figure 2:
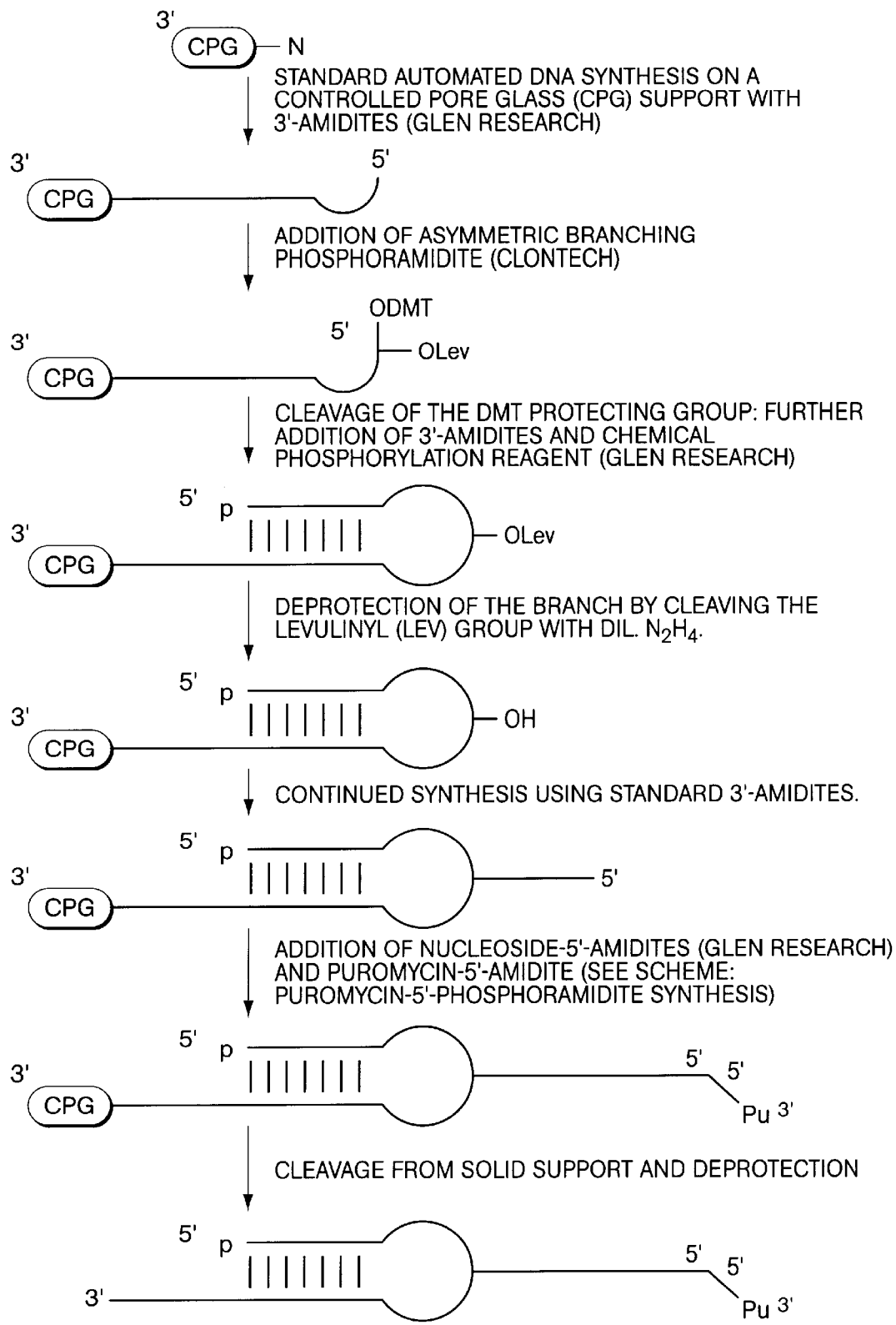
FIG. 2 is a schematic illustration of a method for the generation of branched hairpin structures.

Type A1
Template-Directed Ligation of a Puromycin-Modified Hairpin-Like Structure to an mRNA According to a first exemplary approach, DNA-protein fusions are generated by ligating a puromycin-modified DNA hairpin-like structure to an mRNA molecule, as illustrated in FIG. 1. The first step of this procedure is the attachment of puromycin to the hairpin, and this may be accomplished by a number of techniques, one of which is shown in FIG. 2. By this approach, a DNA hairpin is synthesized with a puromycin-terminated side chain branching out from the DNA molecule. This construct may be generated using an asymmetric branched phosphoramidite (Clontech, Palo Alto, Calif.) in any standard automated DNA synthesis of the hairpin structure (see, for example, User Guide to Expedite Nucleic Acid Synthesis System, Perseptive Biosystems, Framingham, Mass.), followed by the addition of a 5'-phosphate using a chemical phosphorylation reagent (Glen Research, Sterling Va.).

Figure 3:
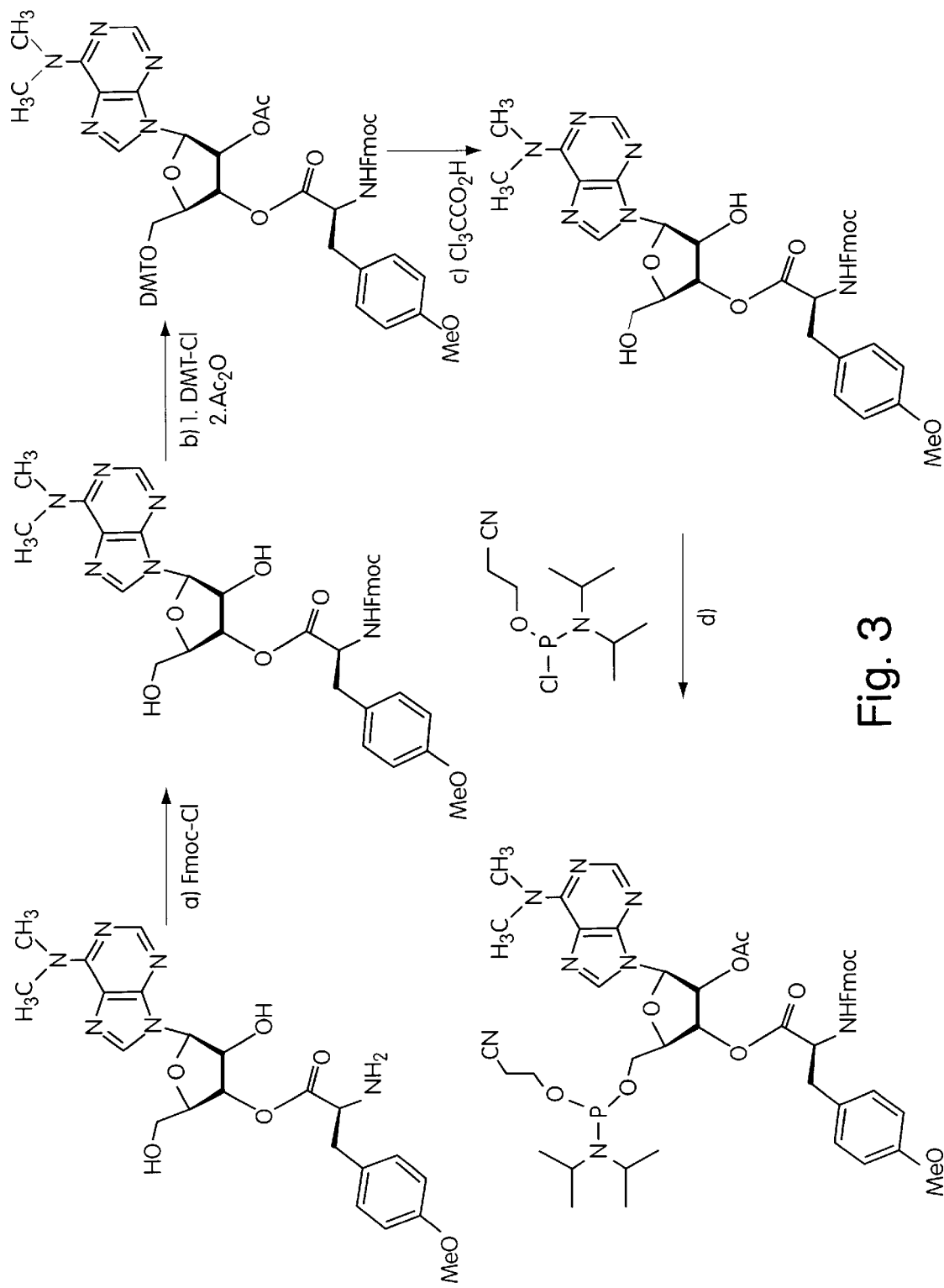
FIG. 3 is a schematic illustration of a method for the synthesis of puromycin-5'-phosphoramidite.

Subsequently the protecting group is selectively removed from the branch (Product Protocol for Asymmetric Branching Phosphoramidite, Clontech, Palo Alto, Calif.), followed by the attachment of the linker portion through standard automated DNA synthesis. Before reaching the end of the linker, the strand orientation is reversed by the addition of a few 5'-phosphoramidites (Glen Research, Sterling, Va.). Finally, the synthesis is terminated through attachment of the puromycin-5'-phosphoramidite, preferably using the synthetic technique shown in FIG. 3. In FIG. 3, steps (a)–(c) may be carried out as described in Greene & Wuts (Protective Groups in Organic Synthesis, $2^{nd}$ ed. (1991) John Wiley & Sons, Inc., New York, N.Y.), and step (d) may be carried out as described in Beaucage (Methods in Molecular Biology, vol. 20, Protocols for Oligonucleotides and Analogs, ed. S. Agarwal (1993) Humana Press, Totowa, N.J., pp. 33–61).

Figure 4:
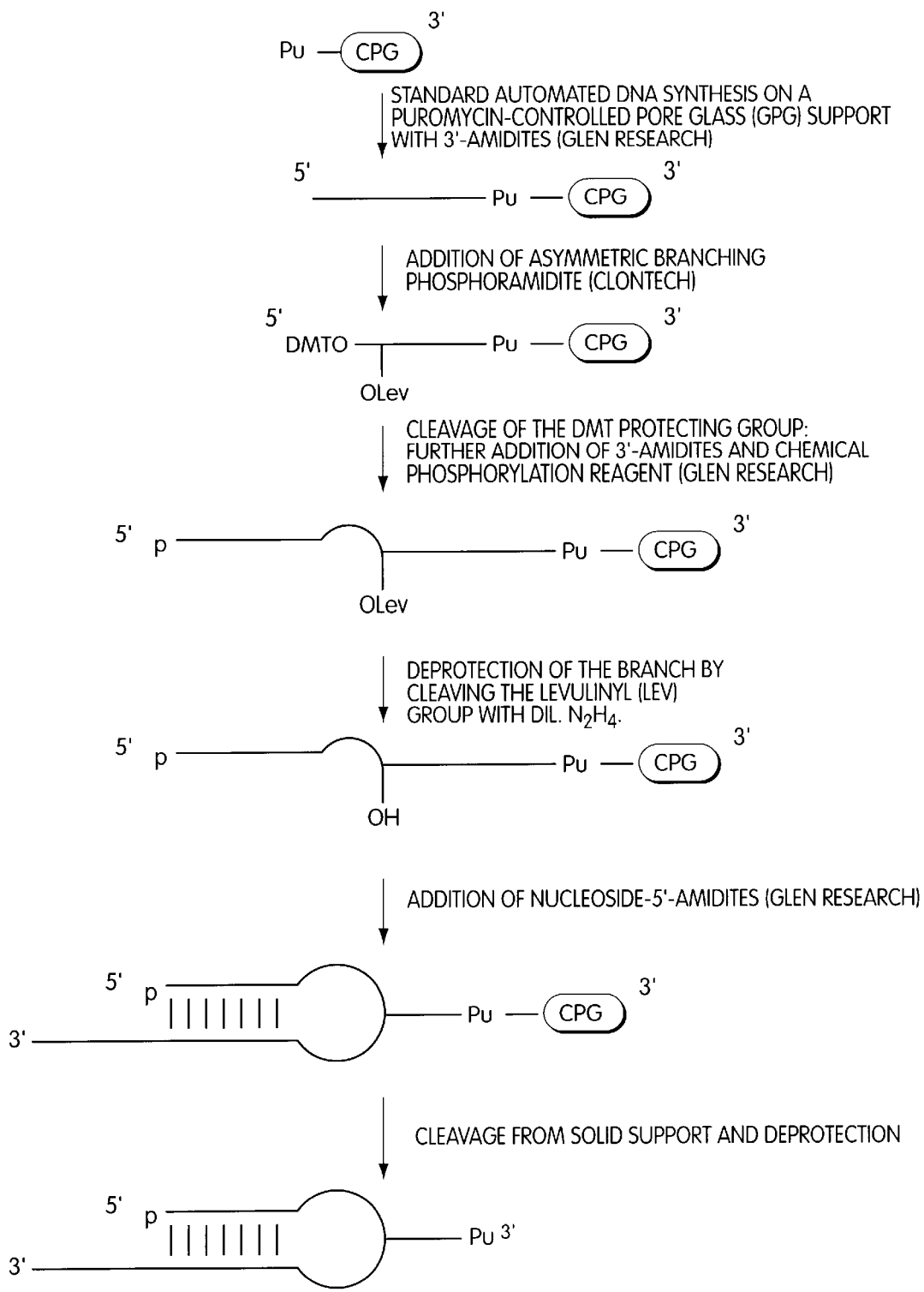
FIG. 4 is a schematic illustration of a method for the generation of branched hairpin structures.

Alternatively, the puromycin-modified branched hairpin may be synthesized as shown in FIG. 4. By this technique, synthesis is initiated from a puromycin-CPG solid support (Glen Research, Sterling, Va.) by first synthesizing the linker portion, followed by incorporation of the branched amidite (Clontech, Palo Alto, Calif.) and addition of the 5'-portion of the hairpin. After deprotection of the branch, the 3'-arm of the hairpin is added by using nucleoside-5'-phosphoramidites (Glen Research, Sterling, Va.).

By either of the above approaches, in the next step, the mRNA is ligated to the hairpin, for example, using T4 DNA ligase and the 3'-overhang as a template (Sambrook, Fritsch & Maniatis Molecular Cloning (1989) Cold Spring Harbor Laboratory Press, Cold Spring Harbor, N.Y.). Ribosomal translation of the RNA then leads to protein synthesis with subsequent fusion formation (see, for example, Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297–12302). In one particular embodiment, the branching point is located in the loop region of the hairpin. Other positions of the branching point (e.g., within the stem structure) may also be utilized. In addition, while a $dA_n$ linker of between approximately 10–60 nucleotides, and more preferably approximately 30 nucleotides, is utilized, both the length and the chemical composition (e.g., PEG (Glen Research, Sterling, Va.) rather than $dA_n$) of the linker may be optimized.

In a final step, the RNA portion of the construct is reverse transcribed into cDNA (for example, as described in Sambrook, Fritsch & Maniatis, Molecular Cloning, (1989) Cold Spring Harbor Laboratory Press, Cold Spring Harbor, N.Y.) using the hairpin 3' end as a primer. Optional digestion of the mRNA by RNase H (see, for example, Sambrook, Fritsch & Maniatis Molecular Cloning, (1989) Cold Spring Harbor Laboratory Press, Cold Spring Harbor, N.Y.) yields a single stranded DNA-protein fusion.

This method also facilitates the formation of truncated DNA transcripts by adding didesoxynucleoside triphosphates during transcription (see, for example, Sanger, Science (1981) vol. 214, p. 1205–1210). Such truncated DNA-protein fusions are useful in protein display experiments (Kuimelis et al., U.S. Ser. No. 60/080,686, filed Apr. 3, 1998), for example, where only the 3'-region of the original message (now the 5'-region of the DNA transcript) is used for hybridization with immobilized oligonucleotide probes.

Type A2
Crosslinking of a Puromycin-Modified Linker to a Primer DNA

Figure 5:
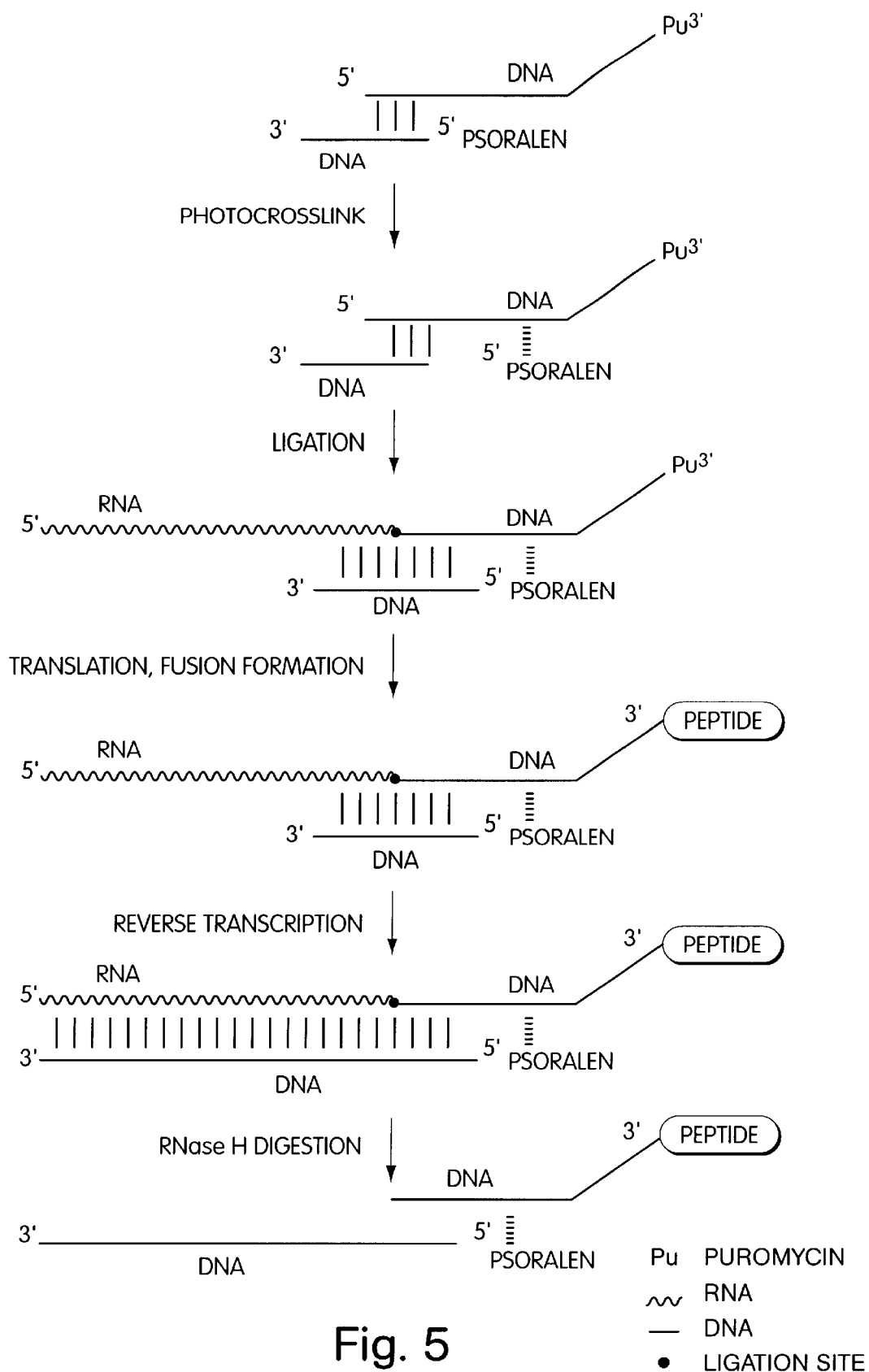
FIG. 5 is a schematic illustration of a method for the generation of DNA-protein fusions that involves photocrosslinking of a 5'-psoralen-modified primer DNA to a suitable linker that bears a 3'-puromycin.

As an alternative to the hairpin-like construct described above, a closely related structure may also be prepared through photocrosslinking of a 5'-psoralen-modified primer DNA with a suitable linker that bears a 3'-puromycin. An exemplary crosslinking method is illustrated in FIG. 5. In this method, the puromycin-bearing linker may be constructed as described, for example, in Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297–12302. The psoralen-modified primer may be generated and the photocrosslinking step carried out as described, for example, in Pieles & Englisch, Nucl. Acids Res. (1989) vol. 17, p. 285–299. The remaining steps may be carried out as described above. This approach does not require the use of non-standard nucleoside/puromycin-5'-phosphoramidites (i.e., which were used during the automated synthesis of the hairpin-linker structure), providing an advantage over the hairpin method. Again, as above, while a $dA_n$ linker of between approximately 10–60 nucleotides, and more preferably approximately 30 nucleotides, is utilized, both the length and the chemical composition (e.g., PEG (Glen Research, Sterling, Va.) rather than $dA_n$) of the linker may be optimized.

Figure 6:
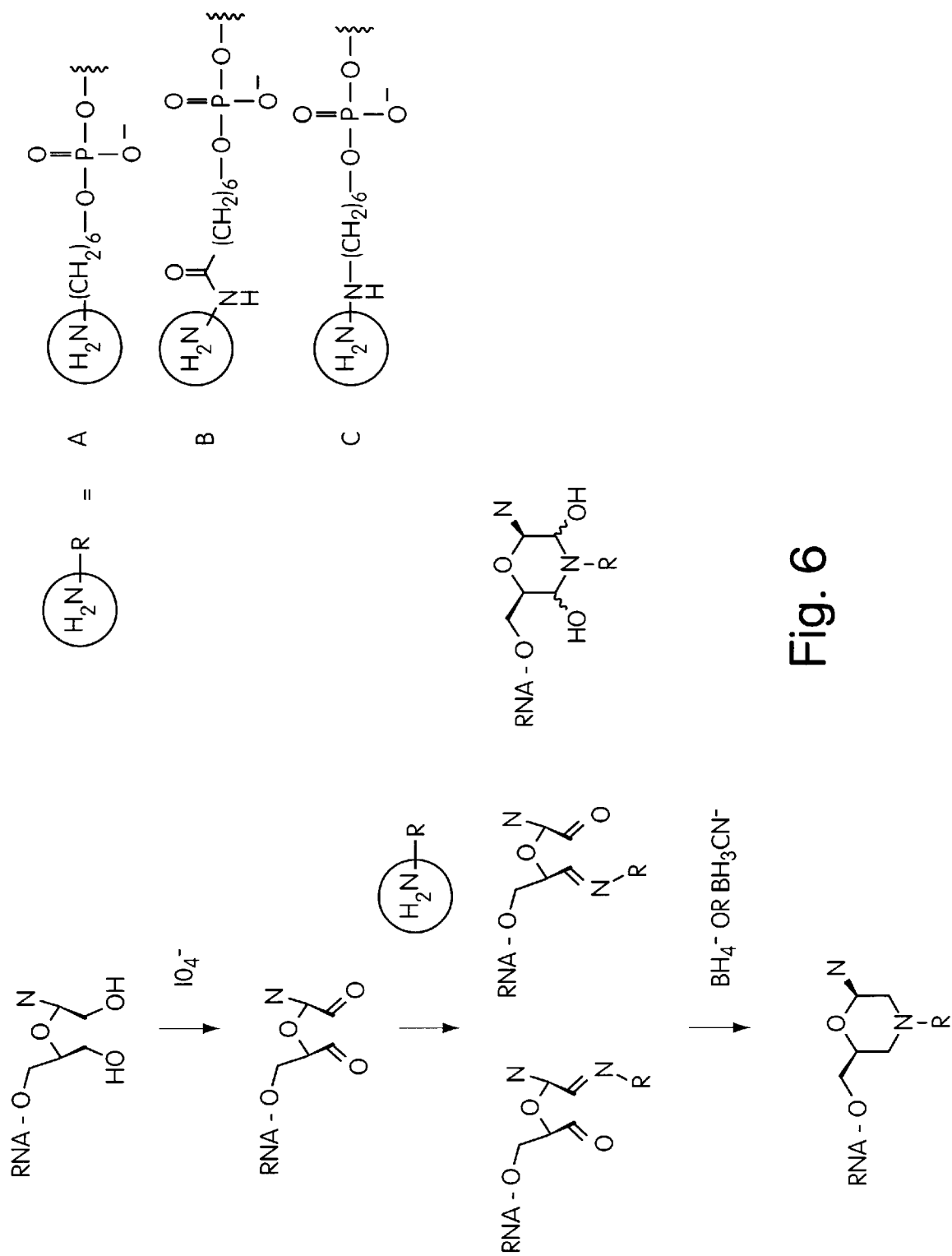
FIG. 6 is a schematic illustration of exemplary methods for the chemical ligation of mRNA and DNA molecules.
Figure 7:
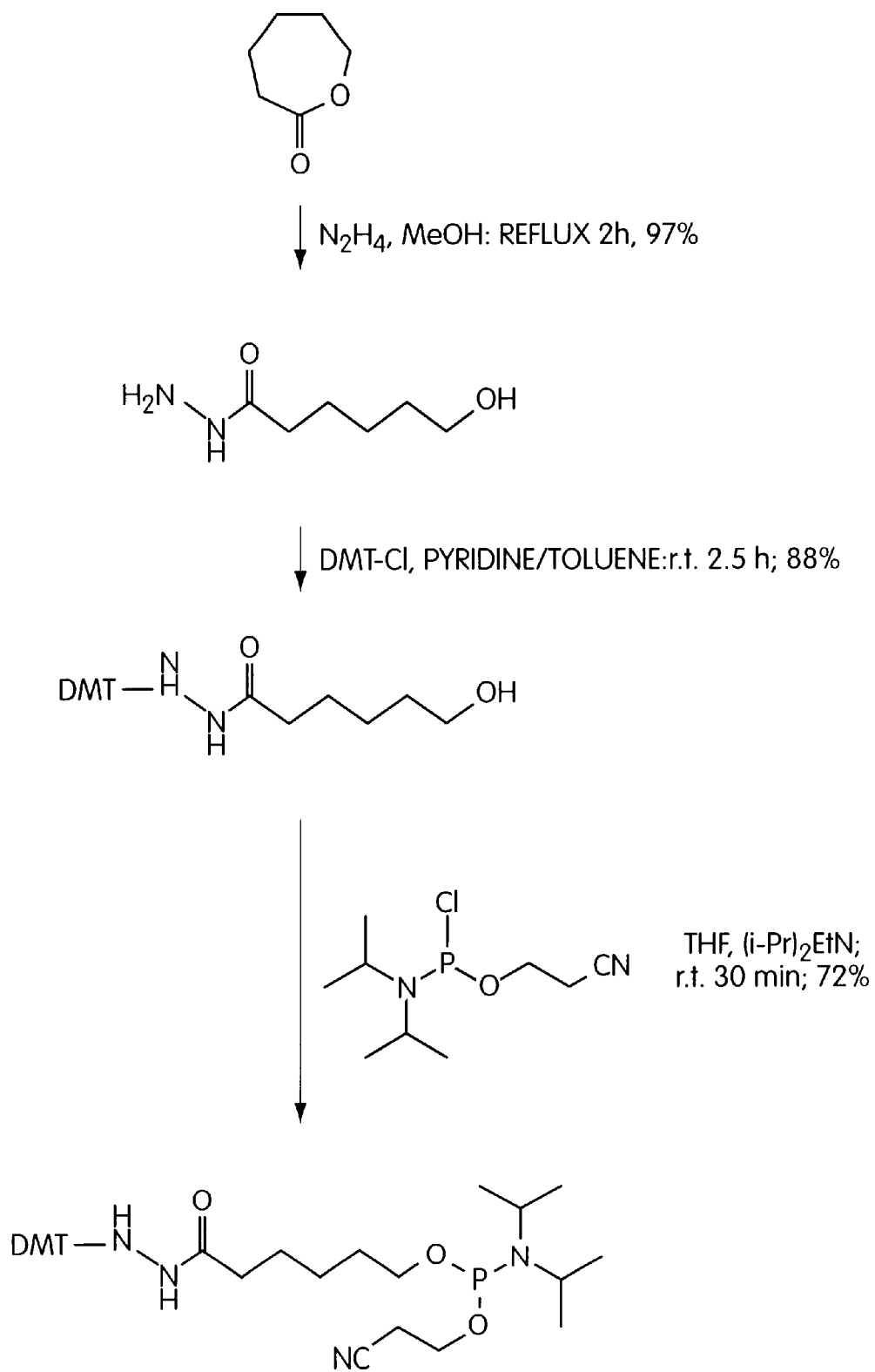
FIG. 7 is a schematic illustration of a method for the synthesis of hydrazide phosphoramidite.
Figure 8:
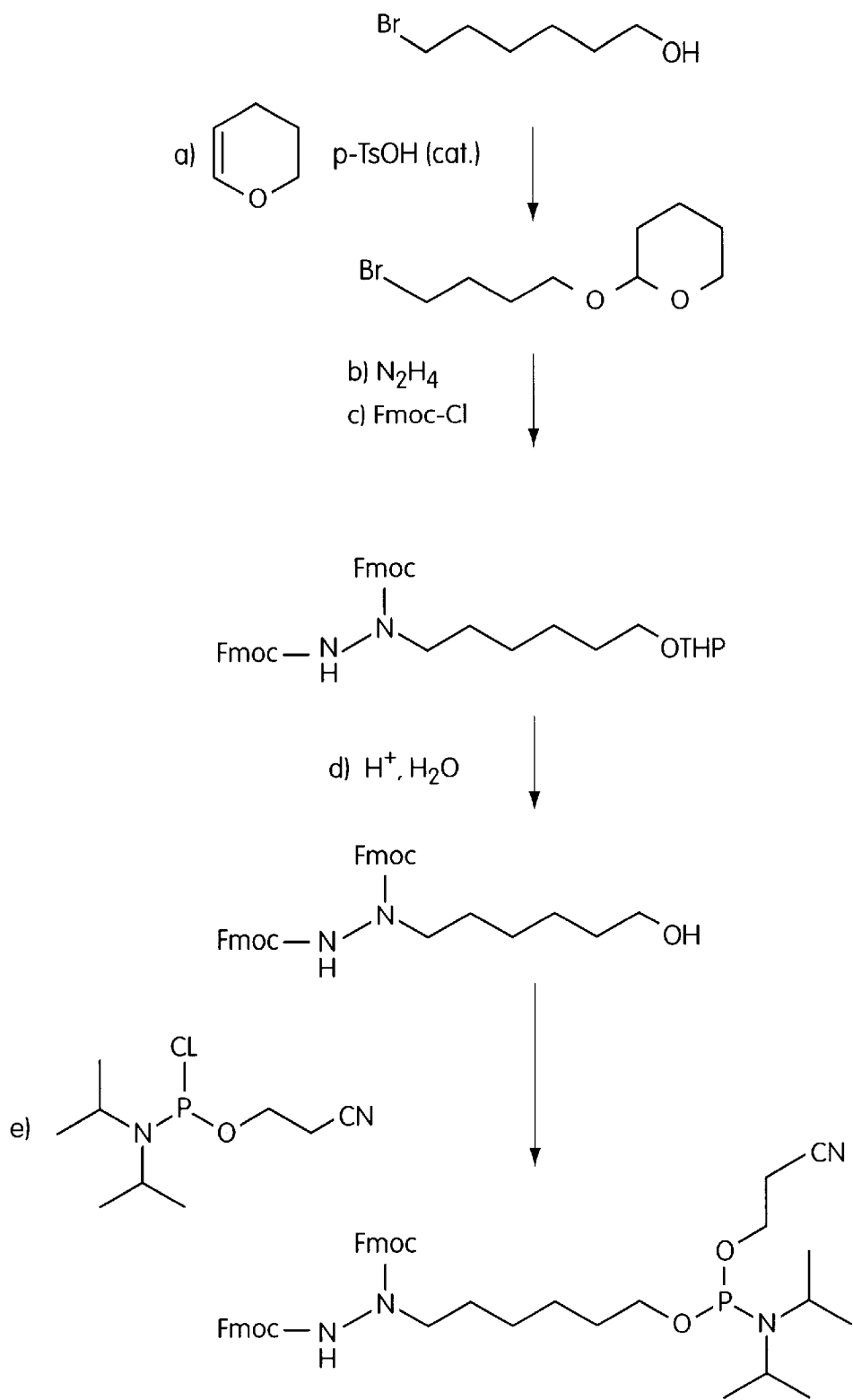
FIG. 8 is a schematic illustration of a method for the synthesis of hydrazine phosphoramidite.

In addition, for each of the Type A1 and Type A2 methods, the ligation reaction between the mRNA and the DNA portion of the construct may be carried out by several alternative techniques. For example, in addition to the enzymatic ligation with T4 DNA ligase described above, this step may be accomplished using chemical methods. In one particular example, the 5'-end of the hairpin may be modified with one (or multiple) amino-groups using the appropriate phosphoramidite (Clontech, Palo Alto, Calif.). After periodate oxidation of the 3'-end of the RNA, the two substrates may be joined through a reductive amination reaction. This is illustrated as scheme "A" in FIG. 6 and is described, for example, in Lemaitre et al., Proc. Natl. Acad. Sci. USA (1987) vol. 84, p. 648–652. Alternatively, this chemical ligation step may involve carbohydrazide or hydrazine modified structures for hydrazone formation or reductive amination. These approaches are illustrated in FIG. 6, respectively, as schemes "B" and "C" and are described, respectively, in Gosh et al. (Anal. Biochem. (1989) vol. 178, p. 43–51) and Proudnikov & Mirzabekov (Nucl. Acids Res. (1996) vol. 24 p. 4535–4542). Hydrazide phosphoramidite synthesis may be carried out as shown in FIG. 7, and hydrazine phosphoramidite synthesis as shown in FIG. 8 and as described in Greene & Wuts (Protective Groups in Organic Synthesis, $2^{nd}$ ed. (1991) John Wiley & Sons, Inc., New York, N.Y. (steps (a) and (c)), Proudnikov & Mirzabekov (Nucl. Acids Res. (1996) vol. 24 p. 4535–4542 (step b)), and Beaucage (Methods in Molecular Biology, vol. 20, Protocols for Oligonucleotides and Analogs, ed. S. Agarwal (1993) Humana Press, Totowa, N.J., pp. 33–61 (step (e)).

Types B1–B3
Chemical Crosslinking to the 3'-end of an mRNA

Yet another approach to the generation of DNA-protein fusions involves the chemical crosslinking of a puromycin-modified linker to the 3'-end of an mRNA molecule. Such crosslinking may be accomplished by a number of approaches.

Figure 9:
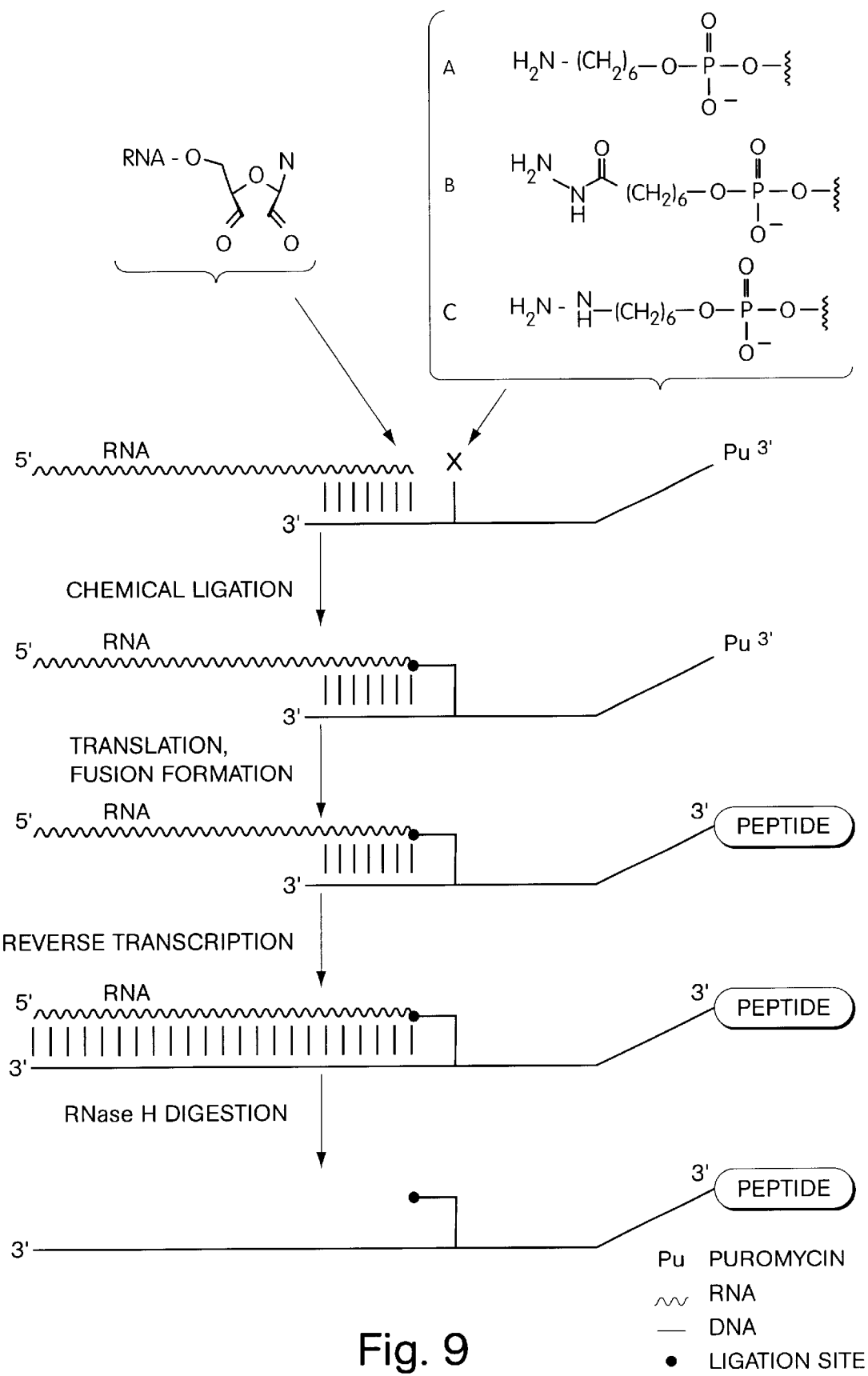
FIG. 9 is a schematic illustration of a method for the generation of DNA-protein fusions that involves chemical crosslinking of a puromycin-modified linker to the 3'-end of an mRNA molecule.

One exemplary approach is shown schematically in FIG. 9. In this approach ("B1"), an oligonucleotide is synthesized that bears a reactive group (e.g., one of the amino derivatives, hydrazides, or hydrazines described above) located between the primer and the linker regions. Duplex formation of the RNA and the primer site takes place immediately adjacent to this reactive group, which then is allowed to react with the periodate-oxidized 3'-end of the RNA leading to a crosslink (as shown in FIG. 6 and as described above). This reaction may occur through reductive amination (FIG. 6, scheme "A" or "C"; Lemaitre et al., Proc. Natl. Acad. Sci. USA (1987) vol. 84, p. 648–652; Proudnikov & Mirzabekov, Nucl. Acids Res. (1996) vol. 24 p. 4535–4542) or hydrazone formation (FIG. 6, scheme "B"; Gosh et al., Anal. Biochem. (1989) vol. 178, p. 43–51). Following translation and fusion formation (Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297–12302), the primer is extended by reverse transcriptase on the RNA template and an optional RNase H digestion step is carried out, generating the DNA-protein fusion (FIG. 9).

As in methods A1 and A2 above, the strand direction of the linker portion's terminal nucleotides is reversed, which can be accomplished by the use of 5'-phosphoramidites (Glen Research, Sterling, Va.) during synthesis.

Figure 10:
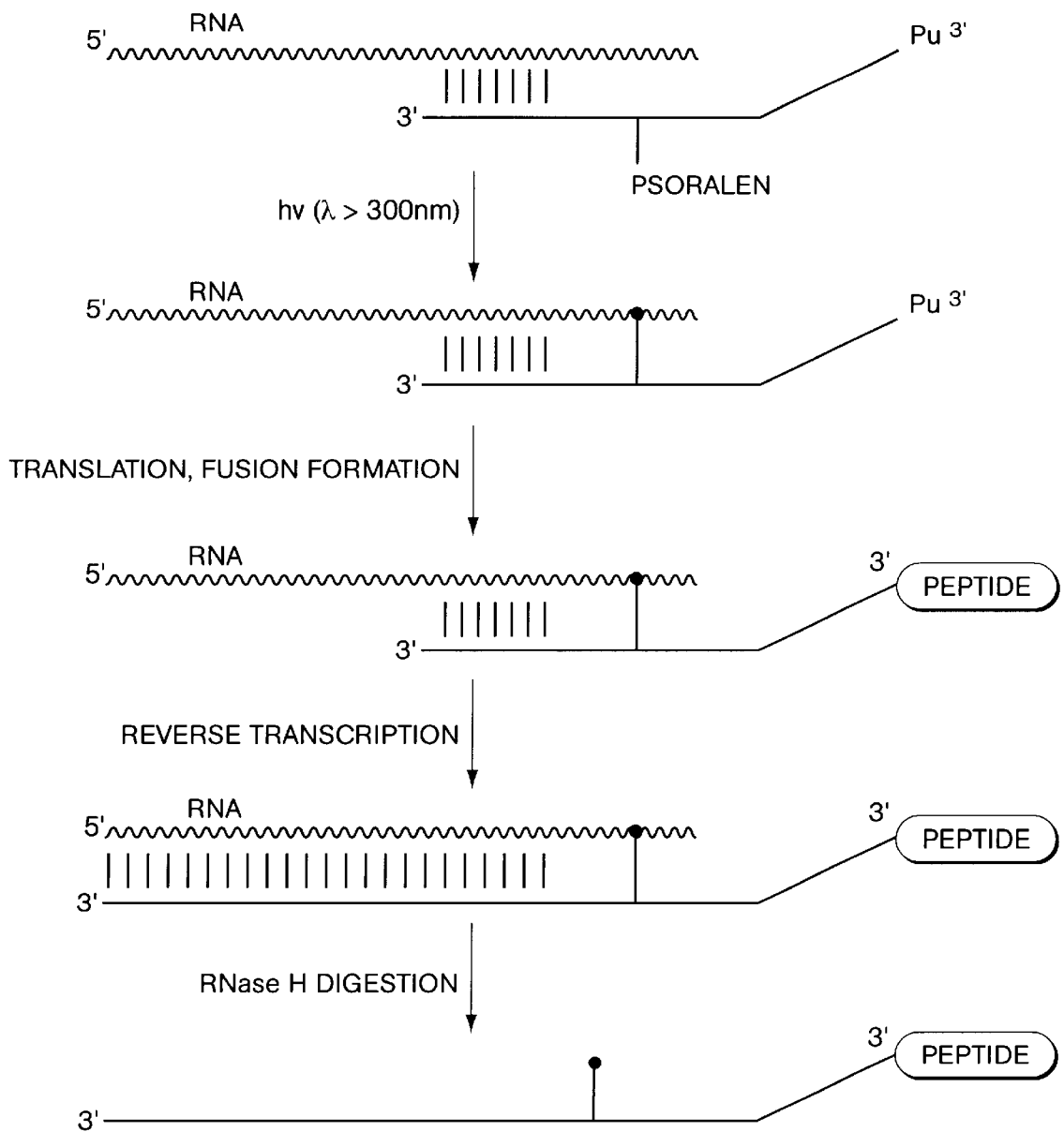
FIG. 10 is a schematic illustration of a method for the generation of DNA-protein fusions that involves psoralen-mediated photocrosslinking of a combined linker/reverse transcription primer construct to the 3'-end of an mRNA molecule.

In yet another exemplary crosslinking approach ("B2"), a photoreactive psoralen moiety is included in the linker as a reactive group (FIG. 10). Such a construct may be synthesized using a psoralen-modified desoxynucleotide phosphoramidite (Pieles et al., Nucleic Acids Res. (1989) vol. 17, p. 8967–8978) or by incorporating a branched phosphoramidite (Clontech, Palo Alto, Calif.) to which a standard psoralen phosphoramidite is attached (Glen Research, Sterling, Va.). Following hybridization of the linker to the target RNA, crosslink formation is achieved through irradiation with UV-light, for example, as described in Pieles and Englisch (Nucl. Acids Res. (1989) vol. 17, p. 285–299). The resulting construct is then subjected to translation and fusion formation (Szostak et al., U.S. Ser. No. 09/007,005 and U.S. Ser. No. 09/247,190; Szostak et al., WO98/31700; Roberts and Szostak, Proc. Natl. Acad. Sci. USA (1997) vol. 94, p. 12297–12302). Reverse transcription and RNase H digestion yields the final DNA-protein fusions.

Figure 11:
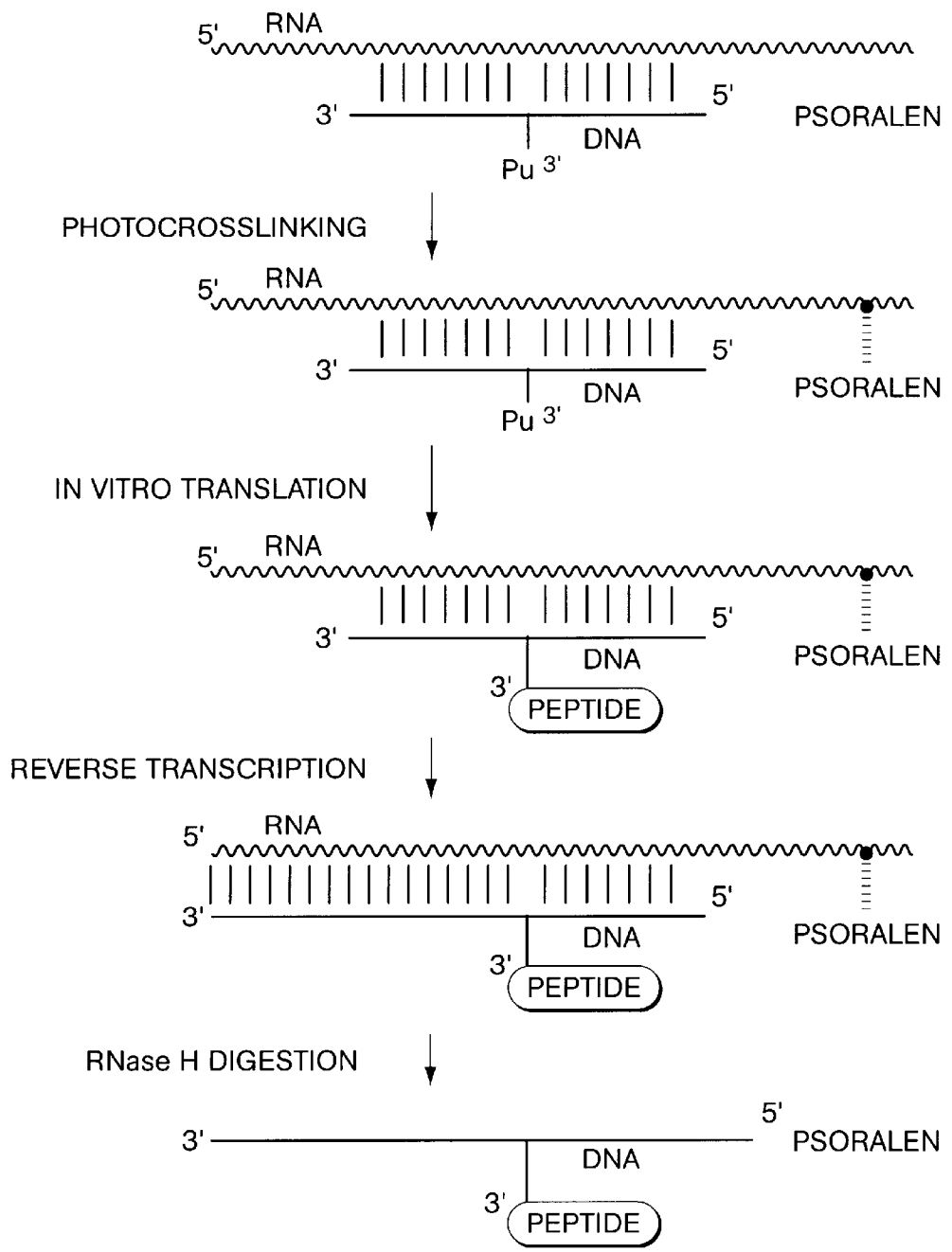
FIG. 11 is a schematic illustration of an alternative method for the generation of DNA-protein fusions that involves psoralen photocrosslinking of a combined linker/reverse transcription primer construct.

Alternatively, crosslinking may be accomplished using a combined linker/reverse transcriptase primer construct as depicted in FIG. 11 ("B3"). In a variant of the above approach, the psoralen moiety is not directly attached between the linker and primer region, but rather connected to a short DNA branch. This DNA portion also hybridizes to the target RNA and thus provides an optimized double-stranded environment for the psoralen to react (Pieles and Englisch, Nucl. Acids. Res. (1989) vol. 17, p. 285–299). Preparation of DNA-protein fusions using this psoralen construct may be carried out as described above.

Figure 12:
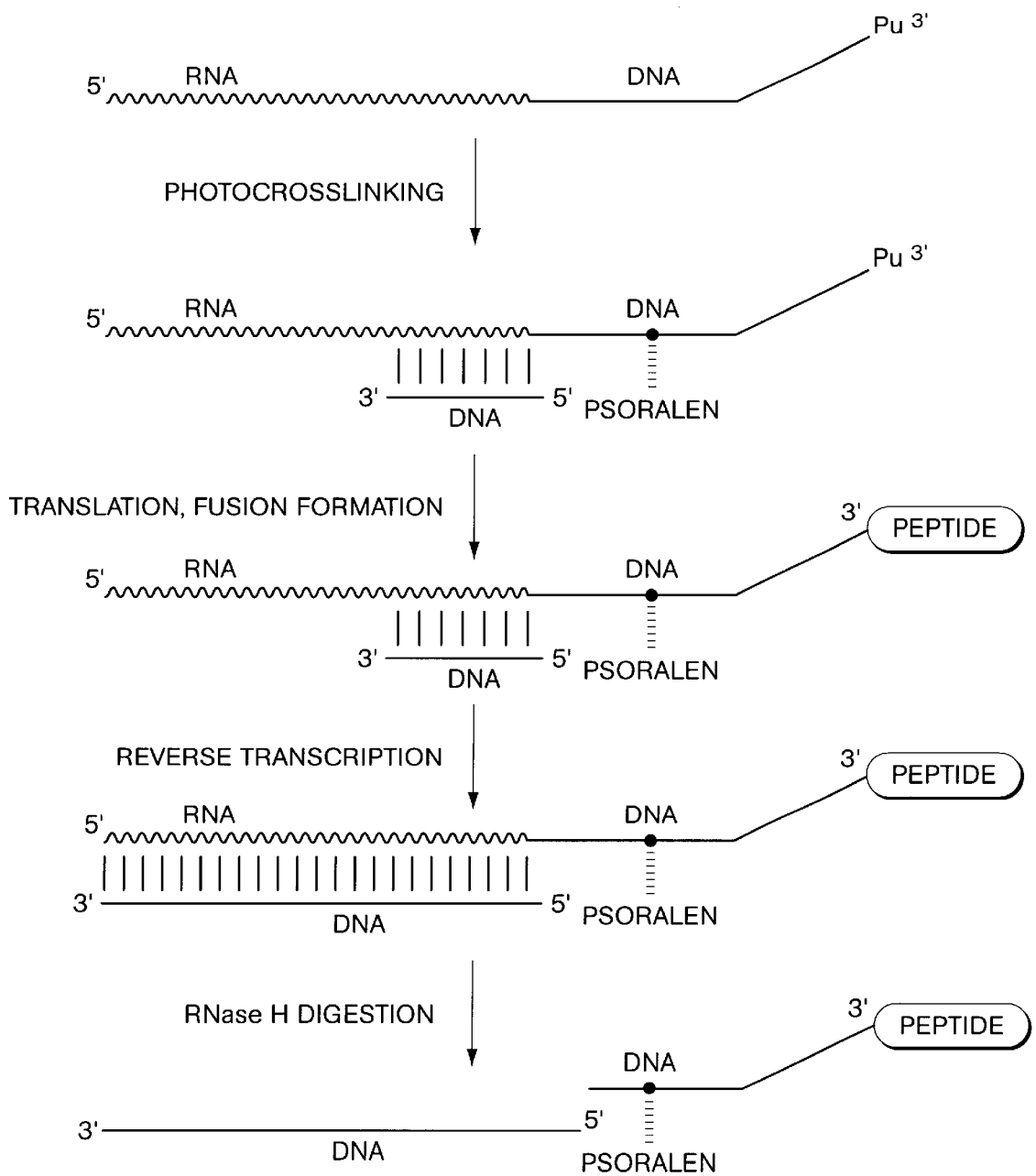
FIG. 12 is a schematic illustration of a method for the generation of DNA-protein ions that involves crosslinking of a reverse transcription primer to a preexisting mRNA-linker construct.

Types C1 and C2
Crosslinking of the Reverse Transcription Primer to Preexisting mRNA-Linker Constructs Another method for generating DNA-protein fusions is shown schematically in FIG. 12. By this approach, RNA is initially ligated to a linker molecule as previously described (Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297–12302). In a subsequent step, a suitable primer bearing a 5'-photocrosslinking reagent (e.g., psoralen, Glen Research, Sterling, Va.) is annealed to the RNA-linker product. Irradiation with light furnishes a covalent crosslink between the two oligonucleotide strands (as described, for example, in Pieles & Englisch, Nucl. Acids Res. (1989) vol. 17, p. 285–299). As in methods Type A1, A2, and B1–B3 above, translation and fusion formation may be carried out, followed by a reverse transcription step and an optional RNase H digestion step to yield DNA-protein fusions (FIG. 12).

Figure 13:
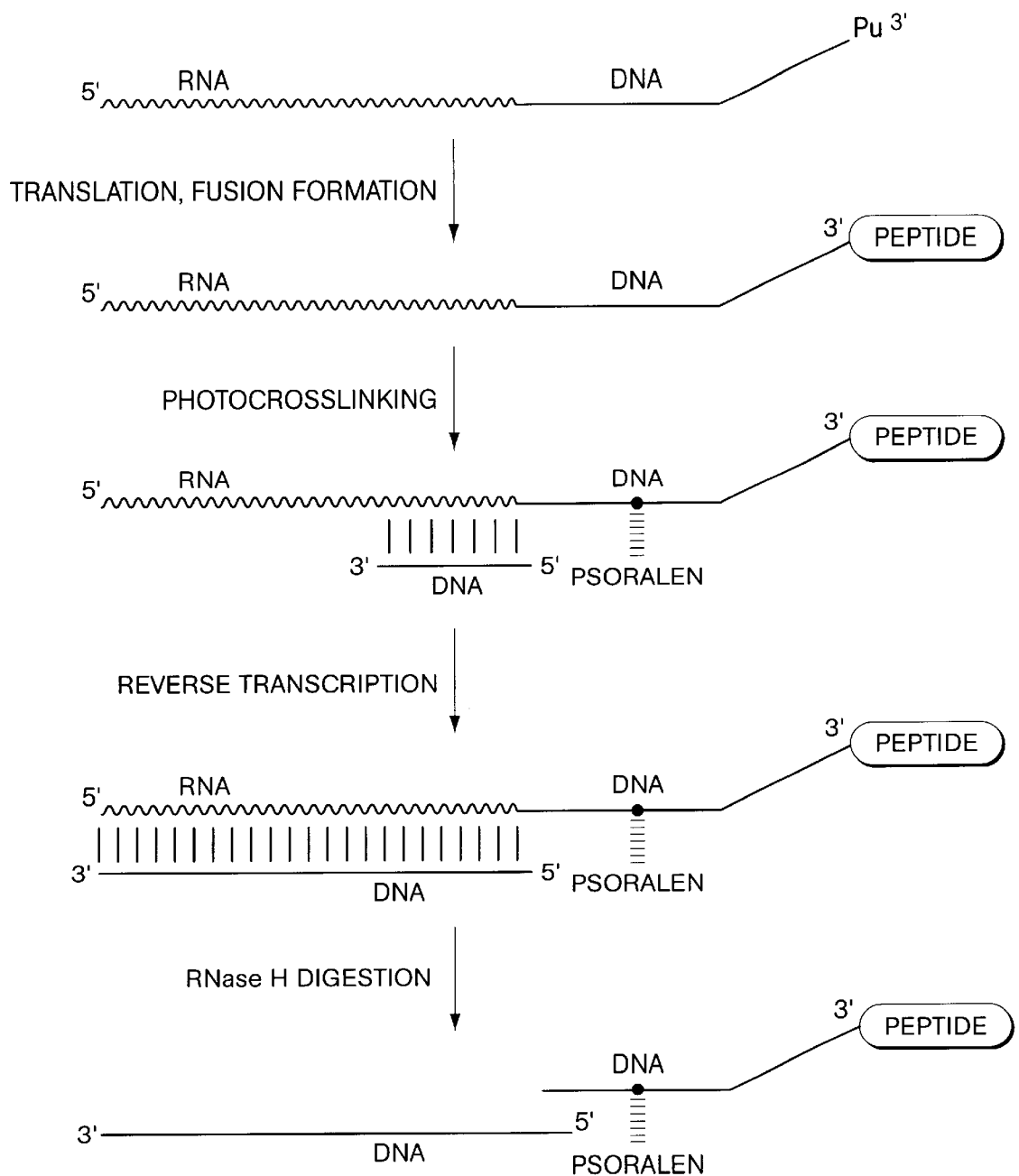
FIG. 13 is a schematic illustration of a method for the generation of DNA-protein fusions that involves crosslinking of a reverse transcription primer to a preexisting mRNA-protein fusion.

Alternatively, as shown in FIG. 13, the initial steps of the above procedure may be carried out in the opposite order. This approach allows translation and fusion formation to be performed prior to crosslinking and reverse transcription. Accordingly, this method allows for the use of previously described and well established reaction conditions and components for translation and RNA-protein fusion formation.

Experimental Results

Figure 14:
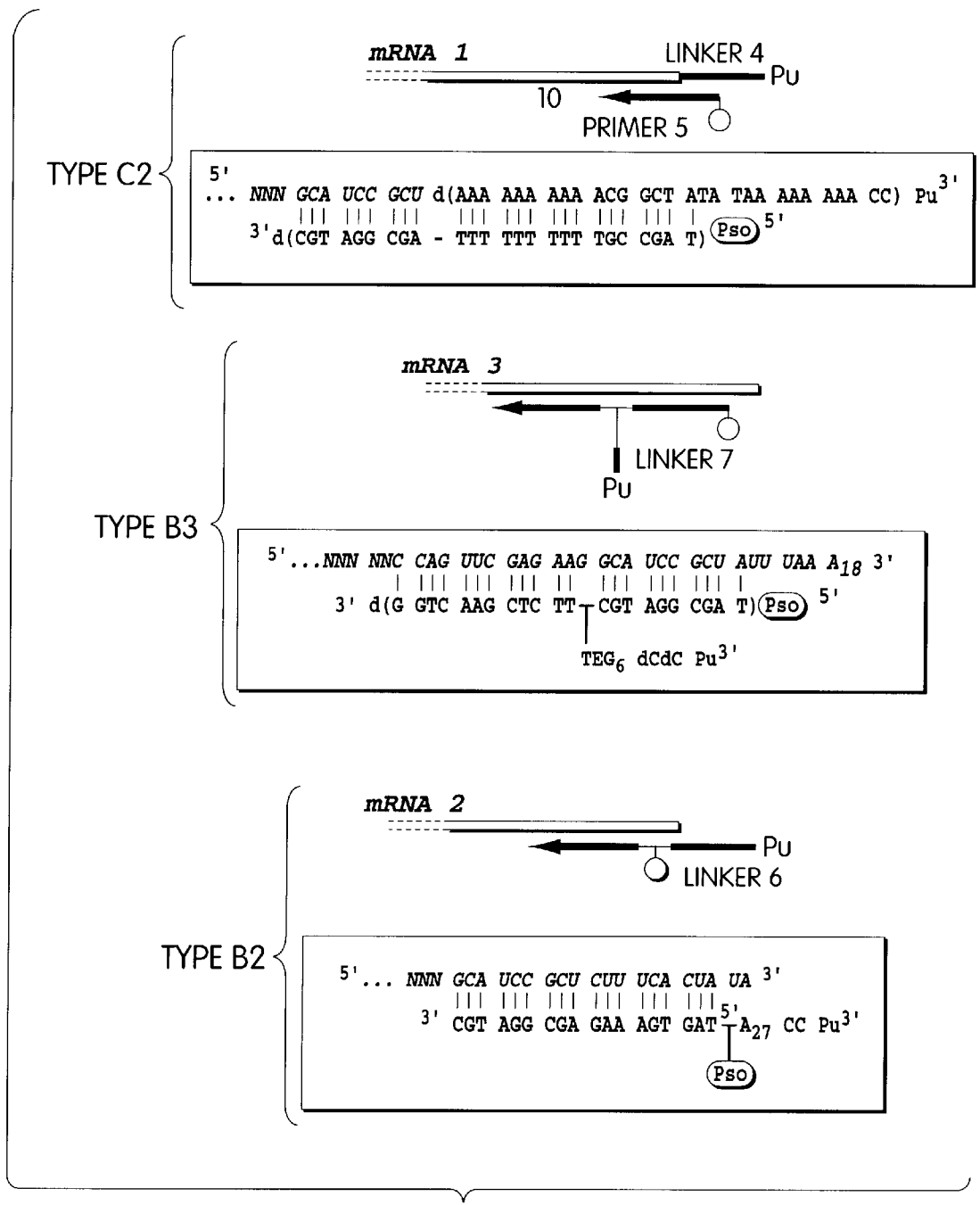
FIG. 14 is a schematic illustration of the oligonucleotide constructs (SEQ ID NOS: 1–6) used for the preparation of the exemplary DNA-protein fusions described herein.

Exemplary techniques described above were carried out to demonstrate DNA-protein fusion formation. These experiments made use of the oligonucleotides depicted in FIG. 14.

Model RNA substrates 1: GGG ACA AUU ACU AUU UAC AAU UAC AAU GGA CUA CAA GGA CGA UGA CGA UAA GGG CGG CUG GUC CCA CCC CCA GUU CGA GAA GGC AUC CGC U (SEQ ID NO: 7); 2: GGG ACA AUU ACU AUU UAC AAU UAC AAU GGA CUA CAA GGA CGA UGA CGA UAA GGG CGG CUG GUC CCA CCC CCA GUU CGA GAA GGC AUC CGC UCU UUC ACU AUA (SEQ ID NO: 8); and 3: GGG ACA AUU ACU AUU UAC AAU UAC AAU GGA CUA CAA GGA CGA UGA CGA UAA GGG CGG CUG GUC CCA CCC CCA GUU CGA GAA GGC AUC CGC UAU UUA AAA AAA AAA AAA AAA AAA A (SEQ ID NO: 9) were synthesized by T7 transcription (Megashortscript transkiption kit, Ambion, Austin, Tex.) using appropriate dsDNA templates. Following transcription, the RNAs were purified by denaturing polyacrylamide gel electrophoresis.

The modified oligonucleotides 4: 5' pd(AAA AAA AAA ACG GCT ATA TAA AAA AAA CC)- Pu (SEQ ID NO: 10); 5: 5' psoralen C2-TAG CCG TTT TTT TTT TAG CGG ATG C (SEQ ID NO: 11); 6: 5' d(cgt agg cga gaa agt gat)-branch [psoralen C6]-d(AAA AAA AAA AAA AAA AAA AAA AAA AAA CC)-Pu (SEQ ID NO: 12); and 7: 5' ggt caa gct ctt-branch[5' psoralen C6-TAG CGG ATG C 3'] spacer$_6$ CC-Pu (SEQ ID NO: 13) [[uppercase=standard DNA-3'-phosphoramidites; lowercase=DNA-5'-phosphoramidites; spacer=spacer-9 phosphoramidite; Pu=puromycin-CPG (all from Glen Research, Sterling, Va.); branch=asymmetric branching amidite (Clontech, Palo Alto, Calif.)] were synthesized on an Expedite Synthesizer Model 8909 (PerSeptive Biosystems, Framingham, Mass.) according to recommended protocols for the corresponding phosphoramidites. For the branched constructs 6 and 7, the main chain was synthesized first and concluded with a final capping step. Next, the levulinyl protecting group was removed from the branching unit through treatment with 0.5 M hydrazine monohydrate in pyridine-acetic acid for 15 minutes at room temperature. Automated synthesis was then resumed and the side chain sequences (indicated in square brackets) were attached. The oligos were fully deprotected in concentrated ammonium hydroxide for 8 hours at 55° C. and purified by denaturing gel electrophoresis.

The DNA sequences 8: d(TTT TTT TTT TAG CGG ATG C) (SEQ ID NO: 14) and 9: d(TAA TAC GAC TCA CTA TAG GGA CAA TTA CTA TTT ACA ATT) (SEQ ID NO: 15) were purchased from Oligos etc. (Wilsonville, Oreg.) and used without further purification.

Type C2 DNA-Protein Fusion Formation

Figure 15:
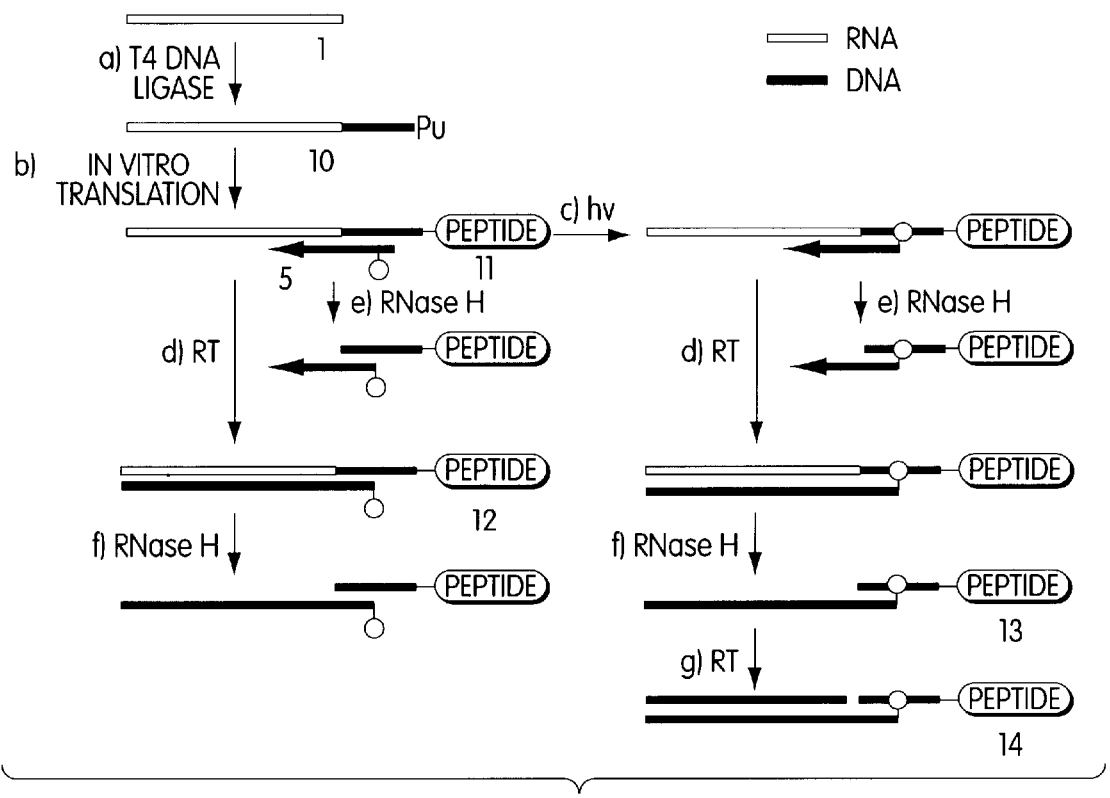
FIG. 15 is a schematic illustration of the preparation of Type C2 DNA-proteins fusions.

Type C2 DNA-protein fusion formation was demonstrated as follows (FIG. 15). RNA 1 and linker 4 were hybridized to template DNA 8 and enzymatically ligated by T4 DNA ligase as previously described (Szostak et al., U.S. Ser. No. 09/007,005 and U.S. Ser. No. 09/247,190; Szostak et al., WO98/31700; Roberts and Szostak, Proc. Natl. Acad. Sci. USA (1997) Vol. 94, p. 12297–12302). After purification by electrophoresis on a denaturing polyacrylamide gel, the resulting mRNA-linker construct was used as a template for in vitro translation using rabbit reticulocyte lysate kits from Ambion. Reaction mixtures contained 50 pmole ligated mRNA 10, 10 mM creatine phosphate, 150 mM potassium acetate, 0.5 mM magnesium chloride, 0.1 mM of each amino acid exept methionine, 150 μCi[$^{35}$S] methionine (Amersham, Arlington Heights, Ill.) and 67% v/v of lysate in a total volume of 300 μl and were carried out for 30 minutes at 30° C. To promote the subsequent fusion formation, KCl and MgCl$_2$ were added to 590 mM and 50 mM final concentrations, respectively, in a volume of 500 μl. Incubation was continued for 60 minutes at 20° C. Products were isolated by diluting the lysate into 10 ml of binding buffer (100 mM Tris pH 8.0, 10 mM EDTA, 1 M NaCl, 0.25% v/v Triton X-100) and adding 10 mg oligo-dT cellulose type 7 (Pharmacia, Piscataway, N.J.). Samples were rotated for 60 minutes at 4° C., and the solid support was then washed with 5 ml ice-cold binding buffer that was devoid of EDTA, followed by elution with 100 μl aliquots of water. Fusion product was found in fractions 2 and 3, and these fractions were combined. The total yield of fusion 11 was determined by scintillation counting of the incorporated [$^{35}$S] methionine to be 1.6 pmole (3.2% of input RNA).

Figure 16:
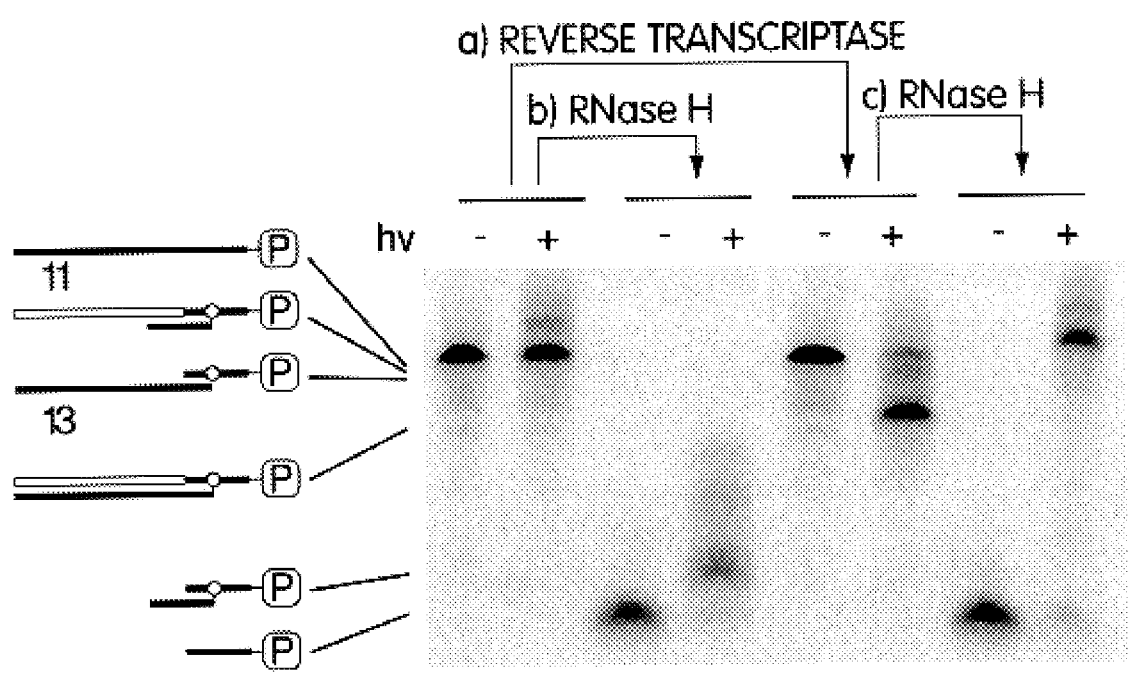
FIG. 16 is a photograph illustrating a product analysis of the Type C2 DNA-protein fusions.

For the conversion of the RNA-protein fusions 11 into DNA-protein fusions 13, the following reactions were performed (FIG. 15). First, 20 μl of the above oligo-dT-purified material 11 was mixed with 0.5 μl primers 5 (50 μM) and 6 μl first strand buffer (Superscript II kit from GibcoBRL; 250 mM Tris-HCl pH 8.3, 375 KCl, 15 mM MgCl$_2$) and briefly heated to 80° C. for 2 minutes, followed by slowly cooling to 0° C. Psoralen photocrosslink formation was induced by irradiating the sample for 15 minutes at 0° C. with λ>310 nm [450 W medium pressure immersion lamp (ACE Glass, Vineland, N.J.) equipped with a Pyrex absorption sleeve in a Quartz immersion well]. Next, 0.6 μl of a dNTP mix (25 mM each), 3 μl of 0.1 M DTT, and 0.4 μl (80 units) Superscript II reverse transcriptase were added, and cDNA synthesis was carried out for 60 minutes at 42° C. The RNA portion was then removed by continuing incubation for 60 minutes at 37° C. after addition of 0.5 μl (1 unit) RNase H (Promega, Madison, Wis.). Finally, double-stranded DNA 14 was generated by adding 50 pmoles of primer 9 and incubating for another 60 minutes at 42° C. Control reactions with non-crosslinked samples were performed as indicated in FIG. 15. Product analysis was performed by electrophoresis on denaturing 6% TBE-Urea gels (Novex, San Diego, Calif.), followed by visualization of the [$^{35}$S]-labelled product bands by exposure on a phosphorimager screen (FIG. 16).

Samples were applied to the gel in the same order as they appear in FIG. 15, beginning with RNA-protein fusion 11 and following the reaction pathway with and without having been photocrosslinked. As indicated in FIG. 16, the gel mobilities correspond well with the expected behavior and clearly confirm the constitution of DNA-protein fusion 13.

Type B3 DNA-Protein Fusion Formation

Figure 17:
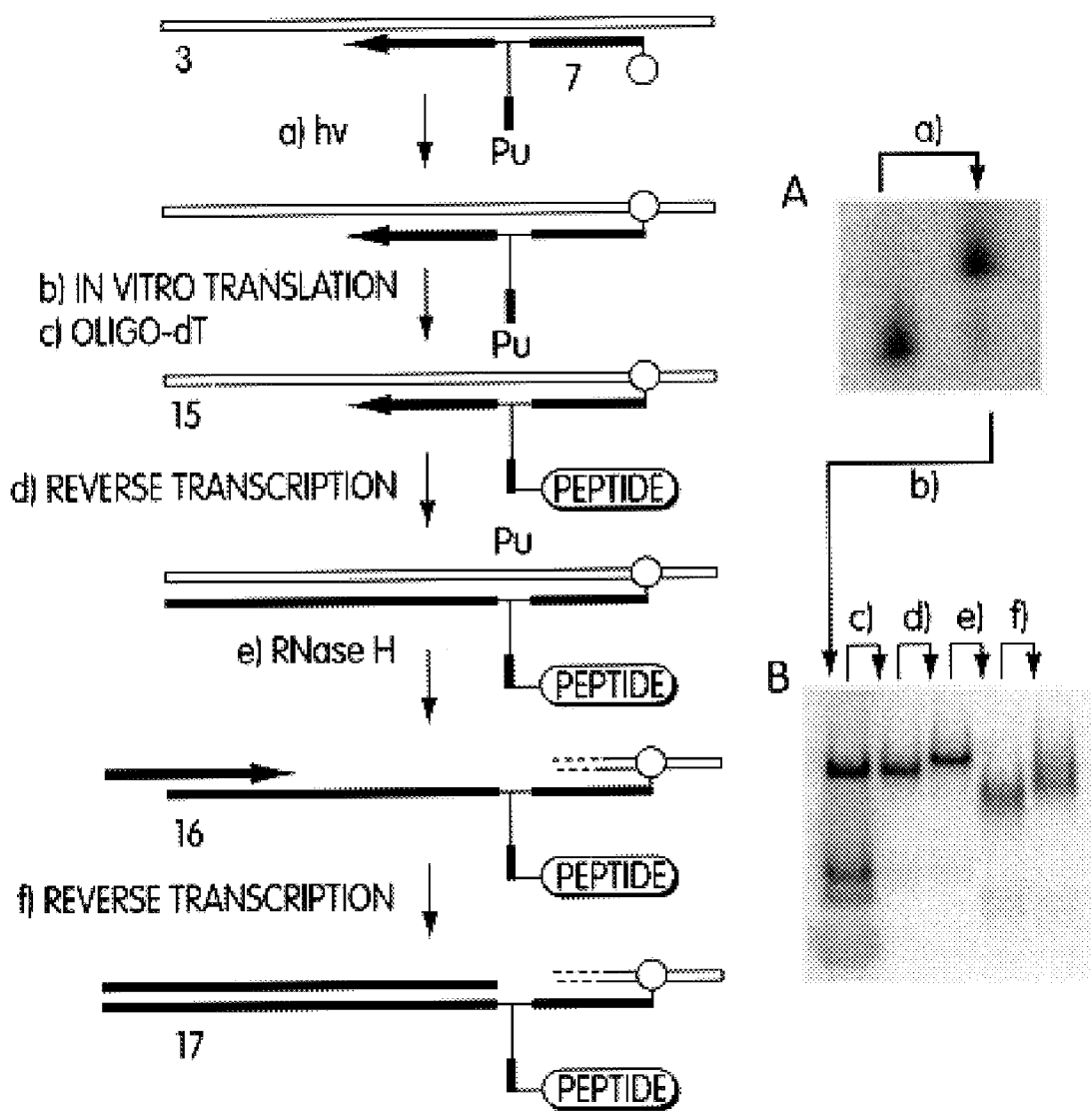
FIG. 17 is a schematic illustration of the preparation of Type B3 DNA-protein fusions.

Type B3 DNA-protein fusion formation was demonstrated as follows (FIG. 17). The branched linker-construct 7 (5 μM) was annealed to the target RNA 3 (2.5 μM) in 25 mM Tris buffer pH 7.0 containing 100 mM NaCl and crosslinked by irradiation for 15 minutes at room temperature in a borosilicate glass vial (Kimble/Kontes, Vineland, N.J.) using a handheld multiwavelength UV lamp model UVGL-25 (UVP, Upland, Calif.) set to long wave. Product analysis was performed by electrophoresis on a 6% TBE-Urea polyacrylamide gel followed by visualization by UV shadowing. These results indicated nearly quantitative conversion of the starting material (gel "A" in FIG. 17). The photoligated product RNA was used for in vitro translation without further separation from remaining unligated RNA and excess linker. In vitro translation and fusion formation reactions were performed as described for Type C2 above, with 100 pmole input RNA in a 300 μl total volume. After purification on oligo-dT cellulose, 5.5 pmole RNA-fusion 15 was obtained. Its conversion into single-stranded and double-stranded DNA-protein fusions 16 and 17, respectively, was done by reverse transcription (Superscript II kit, GibcoBRL, Grand Island, N.Y.) and RNase H (Promega, Madison, Wis.) treatment as described for Type C2 fusions (gel "B" in FIG. 17).

Type B2 DNA-Protein Fusion Formation

Figure 18:
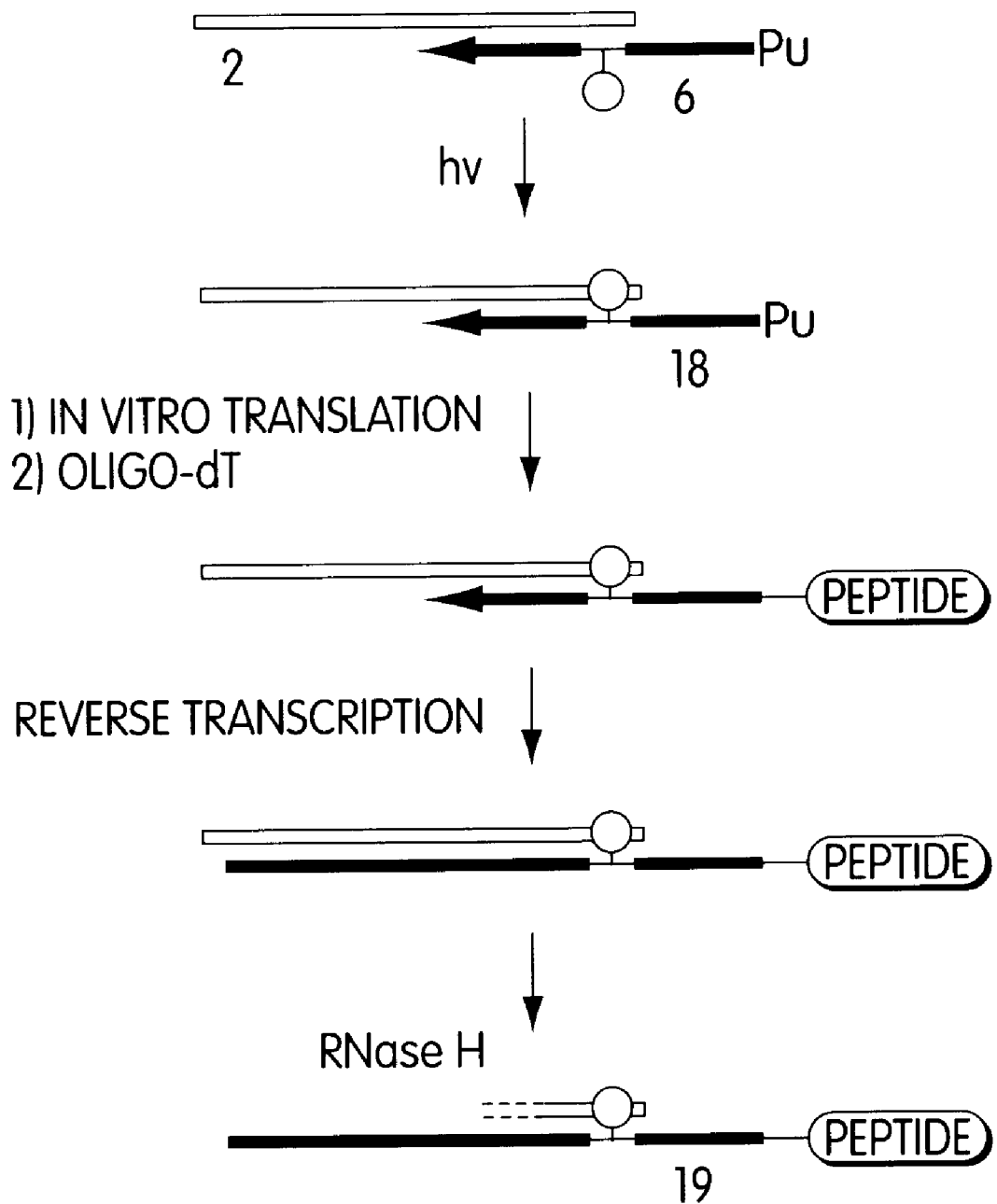
FIG. 18 is a schematic illustration of the preparation of Type B2 DNA-protein fusions.

Type B2 DNA-protein fusion formation was demonstrated as outlined in FIG. 18. Specifically, following the procedure outlined for Type B3 fusions above, RNA 2 was crosslinked to linker 6. Following denaturing polyacrylamide electrophoresis, the ligated product 18 was isolated in 12% yield. In vitro translation, fusion formation, and preparation of DNA-protein fusions 19 were carried out as described for Type B3 fusions above, with similar efficiencies of fusion formation.

DNA-Protein Fusion Stability Tests

Figure 19:
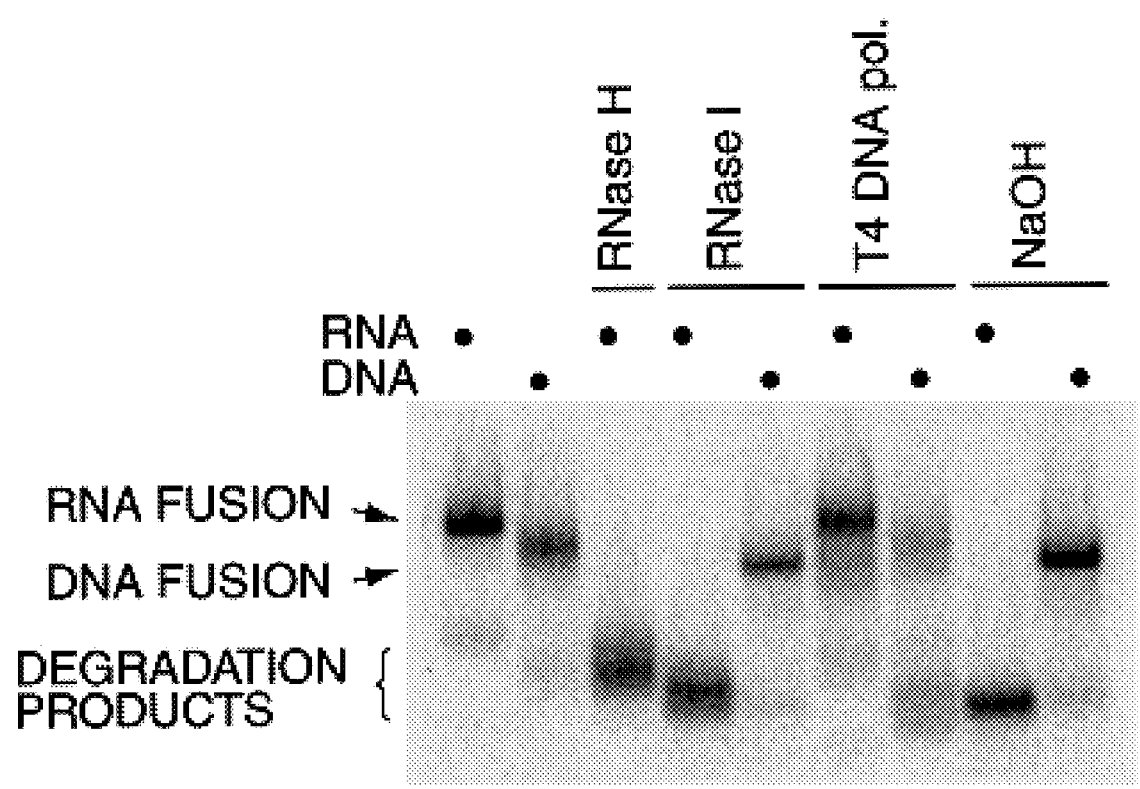
FIG. 19 is a photograph illustrating the resistance analysis of Type B3 DNA-protein fusions against nuclease and base treatment.

To evaluate the nuclease and base resistance of DNA fusions in comparison with the corresponding RNA fusions, the following experiments were carried out. To 10 μl DNA-fusion 16 (Type B3) or RNA-fusion 15 in reverse transcription buffer was added either 0.2 μl (0.4 units) RNase H, 0.2 μl (2 units) RNase I, 0.2 μl (0.6 units) T4 DNA polymerase (3'-5' exonuclease activity), or 2.5 μl of 2.0 M NaOH. Samples were incubated for 30 minutes at 37° C. and then analyzed on a 4–12% NuPage gel (Novex, San Diego, Calif.) followed by autoradiography. Results are shown in FIG. 19 and confirm the increased stability of DNA fusions against ribonucleases and base treatment.

Figure 20:
FIG. 20 is a graph illustrating the experimentally determined half-lives of RNA- and DNA-protein fusion products in the presence of cell membrane preparations.

To test stability of DNA fusion constructs in biological media, 5 nM of either RNA fusions 11 or 12, or DNA fusions 13 or 14 (Type C2) were incubated with 3 μg/μl CHO-K1 cell membranes (Receptor Biology, Beltsville, Md.) in 50 mM Tris-HCl pH 8.3, 75 mM KCl, 3 mM $MgCl_2$, and 10 mM DTT at room temperature. Additional samples of RNA-fusions 11 and 12 were prepared containing 20 mM vanadyl ribonucleside complex ("VRC") to inhibit ribonuclease activity. Aliquots were taken after 0, 5, 15, 30, 60, 120 minutes, and 24 hours and analyzed by electrophoresis on 4–12% NuPage gels (Novex) followed by exposure on a phosphorimager screen. The relative amounts of remaining fusion were plotted against incubation time and half-lives graphically extracted from the resulting curves. As indicated in FIG. 20, all constructs showed more than 50% decay during the initial two hour period except for dsDNA fusion 14, which appeared to be entirely stable under the conditions tested. Following a 24 hour incubation, all fusion constructs were completely degraded due to either nuclease or protease activity.

In Vitro Selection of Desired Proteins

The DNA-protein fusions described herein may be used in any selection method for desired proteins, including molecular evolution and recognition approaches. Exemplary selection methods are described, for example, in Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297–12302; Lipovsek et al., U.S. Ser. No. 60/096,818 and U.S. Ser. No. 09/374,962; and Kuimelis et al. U.S. Ser. No. 60/080,686 and U.S. Ser. No. 09/282,734, all hereby incorporated by reference.

Use

The DNA-protein fusions described herein may be used for any application previously described or envisioned for RNA-protein fusions. Commercial uses include the isolation of polypeptides with desired properties through in vitro evolution techniques (see, for example, Szostak et al., U.S. Ser. No. 09/007,005 and U.S. Ser. No. 09/247,190; Szostak et al., WO98/31700; Roberts & Szostak, Proc. Natl. Acad. Sci. USA (1997) vol. 94, p. 12297–12302)), screening of cDNA libraries that are derived from cellular mRNA (see, for example, Lipovsek et al., U.S. Ser. No. 60/096,818, filed Aug. 17, 1998), and the cloning of new genes on the basis of protein-protein interactions (Szostak et al., U.S. Ser. No. 09/007,005 and U.S. Ser. No. 09,247,190; Szostak et al., WO98/31700), as well as the use of these fusions in protein display experiments (Kuimelis et al. U.S. Ser. No. 60/080,686 and U.S. Ser. No. 09/282,734). In addition, the DNA-protein fusions described herein may be used in binding and molecular recognition assays that involve biological materials that presumably contain ribonucleases, such as whole cells, lysates, or biological fluids. These DNA-protein fusions may be used for any appropriate therapeutic, diagnostic, or research purpose, particularly in the pharmaceutical and agricultural areas.

What is claimed is:

1. A method for generating a DNA-protein fusion, said method comprising:
   (a) covalently bonding a nucleic acid reverse-transcription primer to an RNA, said reverse-transcription primer being bound to a peptide acceptor;
   (b) translating said RNA to produce a protein product, said protein product being covalently bound to said reverse-transcription primer; and
   (c) reverse transcribing said RNA to produce a DNA-protein fusion.

2. A method for generating a DNA-protein fusion, said method comprising:
   (a) generating an RNA-protein fusion;
   (b) hybridizing a nucleic acid reverse-transcription primer to said fusion;
   (c) covalently bonding said primer to said fusion; and
   (d) reverse transcribing the RNA of said RNA-protein fusion to produce a DNA-protein fusion.

3. The method of claim 1 or 2, said method further comprising treating the product of step (c) to remove said RNA.

4. The method of claim 3, wherein said treating comprises contacting the product of step (c) with RNase H under conditions sufficient to digest said RNA.

5. The method of claim 1 or 2, wherein said nucleic acid reverse-transcription primer is a DNA primer.

6. The method of claim 1 or 2, wherein said translating step is carried out in vitro.

7. The method of claim 1 or 2, wherein said peptide acceptor is puromycin.

8. The method of claim 1, wherein said nucleic acid reverse-transcription primer has a hairpin structure.

9. The method of claim 1 or 2, wherein said nucleic acid reverse-transcription primer further comprises a photo-crosslinking agent.

10. The method of claim 9, wherein said photocrosslinking agent is psoralen.

11. The method of claim 9, wherein said crosslinked to an oligonucleotide which is bound to said peptide acceptor.

12. The method of claim 9, wherein said nucleic acid reverse-transcription primer is hybridized to said RNA molecule and said linking step is carried out by photocrosslinking.

13. A method for generating a DNA-protein fusion, said method comprising:
   (a) providing an RNA molecule covalently bonded to a peptide acceptor;
   (b) covalently bonding a nucleic acid reverse-transcription primer to the molecule of step (a);
   (c) translating said RNA molecule to produce a protein, and
   (d) reverse transcribing said RNA molecule to produce a DNA-protein fusion.

14. The method of claim 2 or 13, wherein the protein of said DNA-protein fusion is covalently bonded to the RNA through a non-RNA linker and said nucleic acid reverse-transcription primer is covalently bonded to said linker.

* * * * *

UNITED STATES PATENT AND TRADEMARK OFFICE
CERTIFICATE OF CORRECTION

PATENT NO. : 6,416,950 B1
DATED : July 9, 2002
INVENTOR(S) : Peter Lohse and Markus Kurz It is certified that error appears in the above-identified patent and that said Letters Patent is hereby corrected as shown below:

<u>Title page,</u>
Item [56], U.S. PATENT DOCUMENTS, replace "5,985,757" with -- 5,985,575 --;
OTHER PUBLICATIONS, for "Lemaitre et al.", replace "Vesiclular" with
-- Vesicular --.

<u>Column 4,</u>
Line 58, replace "ions" with -- fusions --.

<u>Column 18,</u>
Line 8, delete "or 2".
Line 17, after "wherein said," add -- primer is photocrosslinking --; and delete "crosslinked".

Signed and Sealed this

Seventeenth Day of June, 2003

JAMES E. ROGAN
*Director of the United States Patent and Trademark Office*

SEQUENCE LISTING

```
<160> NUMBER OF SEQ ID NOS: 15

<210> SEQ ID NO 1
<211> LENGTH: 41
<212> TYPE: DNA
<213> ORGANISM: Artificial Sequence
<220> FEATURE:
<221> NAME/KEY: misc_feature
<222> LOCATION: (1)...(41)
<223> OTHER INFORMATION: n = A,U,C or G
<223> OTHER INFORMATION: Combined DNA/RNA linker/substrate

<400> SEQUENCE: 1
nnngcauccg cuaaaaaaaa aacggctata taaaaaaaac c                           41

<210> SEQ ID NO 2
<211> LENGTH: 25
<212> TYPE: DNA
<213> ORGANISM: Artificial Sequence
<220> FEATURE:
<223> OTHER INFORMATION: DNA linker

<400> SEQUENCE: 2
cgtaggcgat tttttttttg ccgat                                            25

<210> SEQ ID NO 3
<211> LENGTH: 51
<212> TYPE: RNA
<213> ORGANISM: Artificial Sequence
<220> FEATURE:
```

```
<221> NAME/KEY: misc_feature
<222> LOCATION: (1)...(34)
<223> OTHER INFORMATION: n = A,U,C or G
<223> OTHER INFORMATION: Model RNA substrate

<400> SEQUENCE: 3
nnnnnccagu ucgagaaggc auccgcuauu uaaaaaaaaa aaaaaaaaaa a         51

<210> SEQ ID NO 4
<211> LENGTH: 22
<212> TYPE: DNA
<213> ORGANISM: Artificial Sequence
<220> FEATURE:
<223> OTHER INFORMATION: DNA linker

<400> SEQUENCE: 4
ggtcaagctc ttcgtaggcg at                                         22

<210> SEQ ID NO 5
<211> LENGTH: 23
<212> TYPE: RNA
<213> ORGANISM: Artificial Sequence
<220> FEATURE:
<221> NAME/KEY: misc_feature
<222> LOCATION: (1)...(23)
<223> OTHER INFORMATION: n = A,U,C or G
<223> OTHER INFORMATION: Model RNA substrate

<400> SEQUENCE: 5
nnngcauccg cucuuucacu aua                                        23

<210> SEQ ID NO 6
<211> LENGTH: 21
<212> TYPE: DNA
<213> ORGANISM: Artificial Sequence
<220> FEATURE:
<223> OTHER INFORMATION: DNA linker

<400> SEQUENCE: 6
cgtaggcgag aaagtgatac c                                          21

<210> SEQ ID NO 7
<211> LENGTH: 91
<212> TYPE: RNA
<213> ORGANISM: Artificial Sequence
<220> FEATURE:
<223> OTHER INFORMATION: Model RNA substrate

<400> SEQUENCE: 7
gggacaauua cuauuuacaa uuacaaugga cuacaaggac gaugacgaua agggcggcug   60
gucccacccc caguucgaga aggcauccgc u                                 91

<210> SEQ ID NO 8
<211> LENGTH: 102
<212> TYPE: RNA
<213> ORGANISM: Artificial Sequence
<220> FEATURE:
<223> OTHER INFORMATION: Model RNA substrate

<400> SEQUENCE: 8
gggacaauua cuauuuacaa uuacaaugga cuacaaggac gaugacgaua agggcggcug   60
gucccacccc caguucgaga aggcauccgc ucuuucacua ua                    102

<210> SEQ ID NO 9
<211> LENGTH: 115
```

```
<212> TYPE: RNA
<213> ORGANISM: Artificial Sequence
<220> FEATURE:
<223> OTHER INFORMATION: Model RNA substrate

<400> SEQUENCE: 9
gggacaauua cuauuuacaa uuacaauggr cuacaaggac gaugacgaua agggcggcug    60
gucccacccc caguucgaga aggcauccgc uauuuaaaaa aaaaaaaaaa aaaaa        115

<210> SEQ ID NO 10
<211> LENGTH: 29
<212> TYPE: DNA
<213> ORGANISM: Artificial Sequence
<220> FEATURE:
<223> OTHER INFORMATION: DNA linker

<400> SEQUENCE: 10
aaaaaaaaaa cggctatata aaaaaaacc                                      29

<210> SEQ ID NO 11
<211> LENGTH: 25
<212> TYPE: DNA
<213> ORGANISM: Artificial Sequence
<220> FEATURE:
<223> OTHER INFORMATION: DNA linker

<400> SEQUENCE: 11
tagccgtttt tttttagcg gatgc                                           25

<210> SEQ ID NO 12
<211> LENGTH: 47
<212> TYPE: DNA
<213> ORGANISM: Artificial Sequence
<220> FEATURE:
<223> OTHER INFORMATION: DNA linker

<400> SEQUENCE: 12
cgtaggcgag aaagtgataa aaaaaaaaaa aaaaaaaaa aaaaacc                   47

<210> SEQ ID NO 13
<211> LENGTH: 10
<212> TYPE: DNA
<213> ORGANISM: Artificial Sequence
<220> FEATURE:
<223> OTHER INFORMATION: DNA linker

<400> SEQUENCE: 13
tagcggatgc                                                           10

<210> SEQ ID NO 14
<211> LENGTH: 19
<212> TYPE: DNA
<213> ORGANISM: Artificial Sequence
<220> FEATURE:
<223> OTHER INFORMATION: DNA linker

<400> SEQUENCE: 14
tttttttttt agcggatgc                                                 19

<210> SEQ ID NO 15
<211> LENGTH: 39
<212> TYPE: DNA
<213> ORGANISM: Artificial Sequence
<220> FEATURE:
<223> OTHER INFORMATION: DNA linker
```

```
<400> SEQUENCE: 15
taatacgact cactataggg acaattacta tttacaatt                                    39
```